US012636339B2

(12) United States Patent
Callemin et al.

(10) Patent No.: US 12,636,339 B2
(45) Date of Patent: May 26, 2026

(54) HYDROLYZED COLLAGEN FOR USE IN REDUCING BLOOD GLUCOSE

(71) Applicant: ROUSSELOT B.V., Ghent (BE)

(72) Inventors: Kristof Robert Callemin, Ghent (BE); Elien Monique Gevaert, Ghent (BE); Arne Goes, Ghent (BE); Janne Prawitt, Ghent (BE); Sara Vleminckx, Ghent (BE)

(73) Assignee: ROUSSELOT B.V., Ghent (BE)

( * ) Notice: Subject to any disclaimer, the term of this patent is extended or adjusted under 35 U.S.C. 154(b) by 0 days.

(21) Appl. No.: 18/870,747

(22) PCT Filed: Jun. 2, 2023

(86) PCT No.: PCT/EP2023/064848
§ 371 (c)(1),
(2) Date: Dec. 2, 2024

(87) PCT Pub. No.: WO2023/233008
PCT Pub. Date: Dec. 7, 2023

(65) Prior Publication Data
US 2025/0177472 A1     Jun. 5, 2025

(30) Foreign Application Priority Data

Jun. 2, 2022     (BE) .................................. 2022/5427

(51) Int. Cl.
| | |
|---|---|
| A61K 38/01 | (2006.01) |
| A61P 3/10 | (2006.01) |
| C12N 9/48 | (2006.01) |
| C12N 9/50 | (2006.01) |
| C12P 21/06 | (2006.01) |

(52) U.S. Cl.
CPC .............. *A61K 38/014* (2013.01); *A61P 3/10* (2018.01); *C12N 9/485* (2013.01); *C12N 9/50* (2013.01); *C12P 21/06* (2013.01); *C12Y 304/11001* (2013.01); *C12Y 304/17001* (2013.01); *C12Y 304/24* (2013.01)

(58) Field of Classification Search
CPC .................. A61K 38/014; C12N 9/485; C12Y 304/17001; C12Y 304/24; A61P 3/10
See application file for complete search history.

(56) References Cited

U.S. PATENT DOCUMENTS

2013/0303448 A1     11/2013     Sugihara et al.

FOREIGN PATENT DOCUMENTS

| | | | | |
|---|---|---|---|---|
| BR | 112019002725-4 | | 3/2018 | |
| CN | 102911991 A | | 2/2013 | |
| JP | 2009 235064 A | | 10/2009 | |
| JP | 2012 116773 A | | 6/2012 | |
| JP | 5199919 B2 | | 5/2013 | |
| WO | WO-2012102308 A1 * | | 8/2012 | ............... A61P 3/10 |
| WO | WO-2014199780 A1 * | | 12/2014 | ............... A61P 3/10 |

OTHER PUBLICATIONS

International Search Report and Written Opinion for WO 2023/233008 (PCT/EP2023/064848), dated Aug. 23, 2023, pp. 1-12.
Search Report for BE 2022/5427, dated Jan. 3, 2023, pp. 1-13.
International Preliminary Report on Patentability for WO 2023/233008 (PCT/EP2023/064848), dated Jun. 20, 2024, pp. 1-20.
Kehinde Bababode Adesegun et al: "Recently isolated antidiabetic hydrolysates and peptides from multiple food sources: a review", Critical Reviews in Food Science and Nutrition, vol. 60, No. 2, Nov. 21, 2018 (Nov. 21, 2018), pp. 322-340.
Harnedy Padraigin A. et al: "Atlantic salmon (*Salmo salar*) co-product-derived protein hydrolysates: A source of antidiabetic peptides", Food Research International, vol. 106, Apr. 1, 2018 (Apr. 1, 2018), pp. 598-606.
Li-Chan Eunice C. Y. et al: "Peptides Derived from Atlantic Salmon Skin Gelatin as Dipeptidyl-peptidase IV Inhibitors", Journal of Agricultural and Food Chemistry, vol. 60, No. 4, Jan. 20, 2012 (Jan. 20, 2012), pp. 973-978.
Chinese Office Action for Patent Application No. 202380040757.0, dated Mar. 5, 2025, pp. 1-21 (Translation Included).
Brazilian Office Action for Patent Application No. BR112024022789-8, dated Sep. 16, 2025, pp. 1-7 (Translation Not Included).
Brazilian Office Action for Patent Application No. BR112024022789-8, dated Jan. 15, 2026, pp. 1-8 (Translation Not Included).

* cited by examiner

*Primary Examiner* — Gyan Chandra

(74) *Attorney, Agent, or Firm* — Thomas|Horstemeyer, LLP

(57) ABSTRACT

The present invention relates to a hydrolyzed collagen formulation for use in decreasing blood glucose. The hydrolyzed collagen is obtained by enzymatic hydrolysis of a collagen-containing material with a combination of enzymes comprising two or more enzymes selected from the group consisting of a neutral protease, a carboxypeptidase, and an aminopeptidase. The hydrolyzed collagen formulation is particularly suitable as a food supplement, such as for use in ameliorating hyperglycemia and/or a risk factor hyperglycemia.

9 Claims, 5 Drawing Sheets

HYDROLYZED COLLAGEN FOR USE IN REDUCING BLOOD GLUCOSE

CROSS-REFERENCE TO RELATED APPLICATIONS

This application is the National Stage of International Application No. PCT/EP2023/064848, filed Jun. 2, 2023, which claims priority to BE 2022/5427, filed Jun. 2, 2022, all of which are entirely incorporated herein by reference.

FIELD OF THE INVENTION

The present invention relates to an active ingredient and use thereof for ameliorating hyperglycemia and conditions associated with hyperglycemia. The active ingredient of the present invention is suitable as a food supplement.

BACKGROUND OF THE INVENTION

The human body relies on a tight control of its blood glucose level for its normal functioning. A disturbance in the normal blood glucose levels may lead to diseases such as metabolic syndrome, cardiovascular disease, nerve damage, and kidney failure, among others.

Conditions associated with abnormal insulin levels and/or insulin sensitivity (e.g. type 2 diabetes, obesity) are closely linked to the development of hyperglycemia.

The regulation of blood glucose involves the interplay of different organs (e.g. pancreas, brain, liver, gut, adipose and muscle tissue) in part through the release of various hormones. Insulin and glucagon are peptide hormones that counteract each other's actions to balance the blood sugar level. In response to high blood glucose levels, pancreatic beta cells secrete insulin into the blood. This subsequently lowers blood glucose levels by promoting absorption of glucose from the blood into liver, fat and skeletal muscle cells. Glucagon is secreted by pancreatic alpha cells. Glucagon augments the liver to convert stored glycogen into glucose, which is released into the bloodstream.

First line treatment of hyperglycemia initially involves lifestyle changes that may alleviate one or more risk factors of hyperglycemia. These typically include lifestyle changes directed at insulin resistance, diabetes, obesity, or hypertension. Frequently, the lifestyle changes alone are insufficient, which requires metformin and/or insulin treatment to be included as part of the first-line treatment.

In a large group of individuals, the first-line treatment described above does not sufficiently alleviate hyperglycemia. As possible second-line treatment, new classes of glucose-lowering medications are currently being developed and tested (Davies et al. Diabetes Care 2018; 41(12):2669-2701).

New classes of blood glucose-lowering medications include those that target the activity of incretins. Incretins are metabolic hormones that augment the secretion of insulin and/or inhibit the secretion of glucagon in a glucose-dependent manner to decrease blood sugar levels. Glucagon-like peptide-1 (GLP-1) is considered one of the most foremost incretins and therefore is an important target in novel strategies for ameliorating hyperglycemia. Although GLP-1 receptor agonists have demonstrated clinical efficacy (Trujillo et al. Ther Adv Endocrinol Metab. 2021 Mar. 9; 12:2042018821997320), they have several limitations that hamper their widespread use. First, they cause several side effects, including: pancreatitis, pancreatic cancer, or bone disease (Storgaard et al. Diabetes Obes Metab 2017; 19:906-

908), and gastrointestinal related side effects such as nausea, vomiting, and diarrhea. Second, GLP-1 receptor agonist treatment requires repeated subcutaneous injections, which leads to patient discomfort and injection site reactions (Trujillo et al. Ther Adv Endocrinol Metab. 2021 Mar. 9; 12:2042018821997320).

Another example of a new blood glucose-lowering medication is Sitagliptin. Sitagliptin is a selective inhibitor of dipeptidyl peptidase IV (DPPIV). DPPIV effects the hydrolysis of incretin hormones. By doing so, Sitagliptin may increase the plasma concentrations of the active form of incretins such as GLP-1 and gastric inhibitory polypeptide (GIP). This increases insulin release and decreases glucagon concentration. The professional medical practitioner however remains hesitant in prescribing Sitagliptin to a patient. This is largely due to the its several side effects and contra-indications, e.g. up to 10% of patients experience complications such as hypoglycemia, headache, airway infections and nasopharyngitis. Collagen peptides have also been suggested for lowering blood glucose. JP2009235064 describes a blood glucose-lowering collagen peptide obtained by treating starfish with a protease, and JP2012116773 describes an Insulin-like growth factor 1 (IGF-1)-increasing collagen peptide obtainable by treating fish scale and/or fish skin-derived collagen with a proteolytic enzyme.

There remains an unmet need for active ingredients that more effectively and/or more safely ameliorate hyperglycemia. Such an active ingredient may be used in addition or as an alternative to first- and/or second-line treatment of individuals having (or at risk of) hyperglycemia. The present invention aims to provide such an active ingredient.

SUMMARY OF THE INVENTION

The inventors discovered that enzymatic hydrolysis of a collagen-containing starting material with a combination of two or more enzymes selected from the group consisting of a neutral protease, a carboxypeptidase, and an aminopeptidase yields a composition with potent glucose-lowering activity. The glucose-lowering activity appears to be highest when all three of the aforementioned enzymes are used for hydrolysis.

In one aspect, the current invention relates to hydrolyzed collagen for use in decreasing blood glucose, wherein the hydrolyzed collagen is obtained by enzymatic hydrolysis of a collagen-containing material with a combination of enzymes comprising two or more enzymes selected from the group consisting of a neutral protease, a carboxypeptidase, and an aminopeptidase.

In one aspect, the current invention relates to hydrolyzed collagen for (further) use in ameliorating hyperglycemia or a risk factor of hyperglycemia, wherein the hydrolyzed collagen is obtained by enzymatic hydrolysis of a collagen-containing material with a combination of enzymes comprising two or more enzymes selected from the group consisting of a neutral protease, a carboxypeptidase, and an aminopeptidase.

In one aspect, the current invention relates to a method for obtaining hydrolyzed collagen, comprising:
  a) providing a collagen-containing material in a liquid formulation; and
  b) subjecting the collagen-containing material to a combination of enzymes comprising two or more enzymes selected from the group consisting of a neutral protease, a carboxypeptidase, and an aminopeptidase, wherein the hydrolyzed collagen is preferably for use in decreasing blood glucose and/or ameliorating hyperglycemia.

In one aspect, the current invention relates to a hydrolyzed collagen obtainable by the method as disclosed herein, wherein the hydrolyzed collagen is preferably for use in decreasing blood glucose and/or ameliorating hyperglycemia.

DETAILED DESCRIPTION OF THE INVENTION

Aspects of the Invention

In one aspect, the current invention relates to hydrolyzed collagen for use in decreasing blood glucose, wherein the hydrolyzed collagen is obtained by enzymatic hydrolysis of a collagen-containing material with a combination of enzymes, preferably comprising two or more enzymes selected from the group consisting of a neutral protease, a carboxypeptidase, and an aminopeptidase.

In one aspect, the current invention relates to hydrolyzed collagen for use in ameliorating hyperglycemia, wherein the hydrolyzed collagen is obtained by enzymatic hydrolysis of a collagen-containing material with a combination of enzymes, preferably comprising two or more enzymes selected from the group consisting of a neutral protease, a carboxypeptidase, and an aminopeptidase.

In one aspect, the current invention relates to a method for obtaining hydrolyzed collagen, comprising:
  a) providing a collagen-containing material in a liquid formulation; and
  b) subjecting the collagen-containing material to a combination of enzymes, preferably comprising two or more enzymes selected from the group consisting of a neutral protease, a carboxypeptidase, and an aminopeptidase, wherein the hydrolyzed collagen is preferably for use in decreasing blood glucose and/or ameliorating hyperglycemia as taught herein.

In one aspect, the current invention relates to a hydrolyzed collagen obtainable by the method as disclosed herein, wherein the hydrolyzed collagen is preferably for use in decreasing blood glucose and/or ameliorating hyperglycemia as taught herein.

In one aspect, the current invention relates to a method of lowering blood glucose, the method comprising administering a subject a hydrolyzed collagen obtained by enzymatic hydrolysis of a collagen-containing material with a combination of enzymes, preferably comprising two or more enzymes selected from the group consisting of a neutral protease, a carboxypeptidase, and an aminopeptidase.

In one aspect, the current invention relates to a method of treating hyperglycemia or a risk factor of hyperglycemia, the method comprising administering a subject a hydrolyzed collagen obtained by enzymatic hydrolysis of a collagen-containing material with a combination of enzymes, preferably comprising two or more enzymes selected from the group consisting of a neutral protease, a carboxypeptidase, and an aminopeptidase.

In one aspect, the current invention relates to the use of hydrolyzed collagen for the manufacture of a medicament for reducing blood glucose, wherein the hydrolyzed collagen is obtained by enzymatic hydrolysis of a collagen-containing material with a combination of enzymes, preferably comprising two or more enzymes selected from the group consisting of a neutral protease, a carboxypeptidase, and an aminopeptidase.

In one aspect, the current invention relates to the use of hydrolyzed collagen for the manufacture of a medicament for ameliorating hyperglycemia or a risk factor of hyperglycemia, wherein the hydrolyzed collagen is obtained by enzymatic hydrolysis of a collagen-containing material with a combination of enzymes, preferably comprising two or more enzymes selected from the group consisting of a neutral protease, a carboxypeptidase, and an aminopeptidase.

Benefits of the Invention

The use of hydrolyzed collagen, for instance as food supplement, is generally considered safe;

The inventors found that the blood glucose-lowering effect of the hydrolyzed collagen of the invention was similar to that of the medicinal compound Sitagliptin. Hydrolyzed collagen therefore is a valuable addition and/or alternative to glucose-lowering medicinal compounds, because the medicinal compounds generally cause side effects and have contra-indications; and The inventors found that the blood glucose-lowering effect of the hydrolyzed collagen of the invention comprises different mechanisms-of-action. The mechanisms-of-action include increasing Glucagon-like peptide-1 (GLP-1) and inhibiting dipeptidyl peptidase IV (DPP IV). The different effects of hydrolyzed collagen appear to explain the potent blood glucose-lowering activity of hydrolyzed collagen in vivo. Moreover, the presence of different mechanisms-of-action indicates that hydrolyzed collagen may (also) be suitable to treat underling effects of high blood glucose (e.g. in a different population of subjects and/or in different stages of hyperglycemia);

The inventors established the beneficial effects of the hydrolyzed collagen in healthy mice (i.e. showing prevention of hyperglycemia) and obese mice with hyperglycemia (i.e. showing treatment of hyperglycemia). This shows that the hydrolyzed collagen of the invention is effective in ameliorating hyperglycemia as both prevention and treatment.

Blood Sugar and Hyperglycemia

In an embodiment, the current invention relates to a hydrolyzed collagen for use in decreasing blood glucose, wherein the hydrolyzed collagen is obtained by enzymatic hydrolysis of a collagen-containing material with a combination of enzymes, wherein the combination of enzymes comprises two or more enzymes selected from the group consisting of a neutral protease, a carboxypeptidase, and an aminopeptidase.

In a preferred embodiment, the current invention relates to a hydrolyzed collagen for use in decreasing blood glucose, wherein the hydrolyzed collagen is obtained by enzymatic hydrolysis of a collagen-containing material with a combination of enzymes comprising a neutral protease, a carboxypeptidase, and an aminopeptidase.

In a preferred embodiment, the combination of enzymes as disclosed herein comprises a neutral protease, a carboxypeptidase, and an aminopeptidase.

Preferably, the hydrolyzed collagen as disclosed herein is used as an active ingredient. More preferably, the hydrolyzed collagen as disclosed herein is used as an active ingredient in reducing blood glucose as disclosed herein and/or as active ingredient in ameliorating hyperglycemia as disclosed herein.

The term "blood glucose" (i.e. level of glucose in the blood) as used herein may be used interchangeably with "blood sugar". The "blood glucose" is typically, and preferably, expressed as millimoles per liter (mmol/l) and/or as milligrams per deciliter (mg/dl). The blood glucose is usually, and preferably, determined in a fasting individual. In an embodiment, "a fasting individual" means an individual who has not eaten for at least eight hours.

In an embodiment, the hydrolyzed collagen as disclosed herein is for (further) use in ameliorating hyperglycemia.

The term "blood" may herein be used interchangeably with the term "plasma" when referring to a level of a molecule. For example "blood glucose" can also be read as "plasma glucose". For example, "blood GLP-1" can be read also as "plasma GLP-1".

The term "hyperglycemia" as used herein means a high blood glucose. Herein, the normal blood glucose range in fasting individuals is considered to be 80-110 mg/dl. Herein, an individual with a blood glucose level of 126 mg/dl or more is held to have hyperglycemia. An individual in general is held to have impaired glucose tolerance, or pre-diabetes, with a fasting blood glucose of 111-125 mg/dL. Individuals with "impaired glucose tolerance", or "pre-diabetes", are herein considered to have hyperglycemia.

In an embodiment, the "hyperglycemia" as disclosed herein is acute, which is generally characterized by the need for direct administration of insulin.

In an embodiment, the "hyperglycemia" as disclosed herein is chronic, and/or requires prolonged hypoglycemic therapy, either or not in combination with lifestyle changes. The "hyperglycemia" as disclosed herein is preferably chronic hyperglycemia.

In the context of the current invention, a preferred method of measuring hyperglycemia is the haemoglobin A1c (HbA1c) test, which establishes the glycated haemoglobin. The skilled person in the art knows the most-widely accepted and/or most accurate ways of measuring HbA1c, however the preferred analytical methods used for measuring HbA1c include affinity chromatography, immunoassay, cation exchange chromatography, and/or capillary electrophoresis.

In an embodiment, the hyperglycemia as disclosed herein includes "postprandial hyperglycemia". "Postprandial hyperglycemia" is defined in the context of the invention as an excessively high postprandial glucose. As used herein, the term "postprandial glucose level" (PPG level) refers to the amount of glucose in the blood after a meal. In healthy or non-diabetes individuals, levels of blood glucose peak at about an hour after the start of a meal, and usually do not exceed 140 mg/dl, and return to preprandial levels within 2-3 hours. These time-profiles are typically different in diabetic patients or patients suffering a different pathological condition. In an embodiment, the PPG level is measured after 2 hours from the start of the meal, however another time may be more suitable depending on when peak values are typically (or expected to be) located. The acceptable PPG levels, the threshold PPG level defining postprandial hyperglycemia, and the optimal method to measure the PPG level, may vary among medical professional medical practitioners. In the context of the current invention, a PPG level is considered to be excessive/too high (i.e. postprandial hyperglycemia) when it is above 140 mg/dl for an adult below 50 years of age, when it is above 150 mg/dl for an individual between 50-60 years of age, and when it is above 160 mg/dl for an individual of more than 60 years of age.

The present invention may pertain to a non-therapeutic use and/or a therapeutic use of the hydrolyzed collagen, wherein the distinction is based on the level of blood glucose and/or the distinctive groups of subjects experiencing increased blood glucose.

The first group (herein the "group of healthy subjects") comprises healthy persons who do not receive therapeutic benefit from the treatment with the hydrolyzed collagen of the invention, such as when blood glucose levels are not excessive or severe to expect to lead to health issues or (severe) suffering. In addition or alternatively, the blood glucose may have a cause or severity such that the increase in blood glucose naturally disappears over time (i.e. it is not chronic). In addition or alternatively, the blood glucose levels may not be too excessive or severe in the group of healthy subjects, such that they would generally not seek help from a professional medical practitioner.

The second group (herein the "group of pathological subjects") comprises subjects wherein an increase in blood glucose level is of a pathological nature, meaning that the increased blood glucose level typically leads to serious symptoms of pain and (severe) suffering, and/or may lead to (serious) health and psychological risks. In addition, the increased blood glucose may be chronic in the group of pathological subjects. The severity of blood glucose increase is such that help from a professional medical practitioner is generally sought for.

The professional medical practitioner is typically able to determine on a case-by-case basis whether changes in blood glucose levels require a therapeutic or a non-therapeutic intervention (i.e. whether a person falls in the group of healthy subjects or in the group of pathological subjects). The professional medical practitioner may for instance establish whether changes in blood glucose may lead to (serious) health and psychological risks and/or whether it is a chronic change in blood glucose.

Depending on whether an individual is healthy or experiences a medical condition (e.g. hyperglycemia, diabetes, obesity), an amelioration of postprandial glucose can be considered as respectively either a non-therapeutic or therapeutic intervention. In addition or alternatively, depending on the amount of glucose in the blood after a meal, an amelioration of postprandial glucose can be considered as either a non-therapeutic or therapeutic intervention. For instance, in healthy individuals the amount of glucose after a meal typically does not exceed 140 mg/dl, therefore amelioration of a postprandial glucose level below 140 mg/dl could be considered a non-therapeutic intervention. For instance, in individuals experiencing a medical condition (e.g. hyperglycemia, diabetes, obesity), the amount of glucose after a meal typically can be 140 mg/dl or more, therefore amelioration of a postprandial glucose level of 140 mg/dl or more could be considered a therapeutic intervention.

In an embodiment, the hydrolyzed collagen is for use in therapeutic lowering of blood glucose, such as in ameliorating hyperglycemia or a risk factor of hyperglycemia. In an embodiment, the hydrolyzed collagen is for non-therapeutic lowering of blood glucose, such as in ameliorating postprandial glucose.

In an embodiment, the hydrolyzed collagen is for non-therapeutic ameliorating postprandial glucose, wherein the postprandial glucose level is preferably below 140 mg/dl, more preferably below 120 mg/dl, even more preferably below 100 mg/dl (i.e. before start of the intervention with the hydrolyzed collagen). In an embodiment, the hydrolyzed collagen is for therapeutic ameliorating postprandial glucose, wherein the postprandial glucose level is preferably at least 140 mg/dl, more preferably at least 160 mg/dl, even more preferably at least 180 mg/dl (i.e. before start of the intervention with the hydrolyzed collagen).

In an embodiment, the hydrolyzed collagen as disclosed herein is for (further) use in ameliorating a risk factor for hyperglycemia.

The beneficial effect of the hydrolyzed collagen of the invention was demonstrated in healthy mice wherein hyperglycemia was induced after receiving hydrolyzed collagen. The beneficial effect of the hydrolyzed collagen of the invention was also demonstrated in obese mice with hyperglycemia that were administered hydrolyzed collagen. This shows that the hydrolyzed collagen of the invention is effective in both prevention and treatment of hyperglycemia.

In the context of the current invention, the term "ameliorating" encompasses both the "preventing" and the "treating" of a condition. The term "preventing" means to ensure that a subject will not develop a condition (e.g. hyperglycemia or a risk factor for hyperglycemia). An intervention is herein also considered to be a form of "preventing" when a condition is delayed, reduced in severity and/or reduced in incidence, even when the condition is not entirely kept from happening. As used herein, "preventing" or "prevention" by an intervention encompasses the situation wherein a subject previously has experienced a condition (e.g. hyperglycemia or a risk factor for hyperglycemia), but an intervention keeps the condition from recurring. The "preventing" or "prevention" may have a therapeutic and/or a non-therapeutic effect. If the "preventing" or "prevention" is therapeutic in nature, it may be also directed at a symptom of a disease or condition and/or an underlying pathology thereof. The "preventing", or "prevention can be defined by any delay, change in severity, and/or change in incidence, such as of at least 5, 10, 20, 30, 40, 50, 60, 70, 80, 90, 100%, between, as compared to a control or reference as measured by any standard technique. In the context of the current invention "treating" means that an intervention reduces and/or cures a condition (e.g. hyperglycemia or a risk factor for hyperglycemia) once the condition is already existing. The "treating" may have a therapeutic and/or a non-therapeutic effect. If the "treating" is therapeutic in nature, it may be directed at a symptom of a disease or condition and/or an underlying pathology thereof. The treatment can for example be any reduction in severity, incidence, and/or frequency of the condition, such as of at least 5%, 10%, 20%, 40%, 50%, 60%, 80%, 90%, 95%, or 100%, as compared to a control or reference as measured by any standard technique. As used herein, "ameliorating" also encompasses "curing". The term "ameliorating" may herein be used interchangeably with "reducing" or "decreasing".

As used herein, a "risk factor for hyperglycemia" means a condition that is associated with an increased chance of developing hyperglycemia. In individuals with a risk factor for hyperglycemia, it is feasible to administer a blood glucose-lowering agent as prophylaxis in prevention of hyperglycemia. In addition or alternatively, in individuals with a risk factor for hyperglycemia, it is preferably feasible to administer a blood glucose-lowering agent as prophylaxis to ameliorate the hyperglycemia that may develop. For example, obesity is a risk factor for hyperglycemia. The administration of a blood glucose-lowering agent to an obese individual may prevent hyperglycemia in said obese individual and/or ameliorate the hyperglycemia in said individual if it develops.

There may be several risk factors for developing hyperglycemia. In the context of the current invention, too low level of insulin in the body, defect(s) in insulin action, and/or insulin resistance are considered risk factors for hyperglycemia. In the current disclosure, Type 2 diabetes is considered a risk factor for hyperglycemia. In addition or alternatively, one or more of the following conditions are considered herein to be risk factors for developing hyperglycemia: gestational diabetes, high body mass index (BMI), obesity, and hyperglucagonemia.

Several hormones act to increase blood glucose levels hyperglycemia when present in excess and are herein considered risk factors for hyperglycemia, including excess of one or more of: cortisol, catecholamines, growth hormone, glucagon, and thyroid hormones.

In a preferred embodiment, the risk factor for hyperglycemia as disclosed herein is insulin resistance. The term 'insulin resistance' as used herein encompasses all conditions diagnosed as 'insulin resistance' by a professional medical practitioner. The term 'insulin resistance' as used herein preferably refers to peripheral insulin resistance and/or hepatic insulin resistance. Insulin resistance is preferably diagnosed by the gold standard which is the "hyperinsulinemic euglycemic clamp" (DeFronzo R A, Tobin J D, Andres R, Am J Physiol. 1979 September; 237(3):E214-23). This method measures the amount of glucose necessary to compensate for an increased insulin level without causing hypoglycemia. The procedure may take two hours and preferably involves the following steps (or similar steps): Through a peripheral vein, insulin is infused at 10-120 mU per m$^2$ per minute. In order to compensate for the insulin infusion, glucose (20%) is infused to maintain blood sugar levels between 5 and 5.5 mmol/L. The rate of glucose infusion is determined by checking the blood sugar levels every five to ten minutes (Muniyappa R, Lee S, Chen H, Quon M J, January 2008, American Journal of Physiology. Endocrinology and Metabolism. 294 (1): E15-26). The rate of glucose infusion during the last thirty minutes of the test determines insulin sensitivity. If high levels (7.5 mg/min or higher) are required, the patient is insulin sensitive. Low levels (4.0 mg/min or lower) indicate insulin resistance. Levels between 4.0 and 7.5 mg/min are not definitive, and suggest "impaired glucose tolerance," an early sign of insulin resistance.

The homeostatic model assessment for insulin resistance (HOMA or HOMA-IR) is an alternative preferred method to determine and quantify insulin resistance in a fasting steady-state condition, and correlates with the golden standard (See e.g. Matthews D R, Hosker J P, Rudenski A S, Naylor B A, Treacher D F, Turner R C (1985). Diabetologia. 28 (7): 412-9. Doi: 10.1007/BF00280883. PMID 3899825; and/or A. S. Rudenski; D. R. Matthews; J. C. Levy; R. C. Turner (1991) Metabolism. 40 (9): 908-917). A HOMA(-IR) score that deviates from a reference range can indicate insulin resistance. HOMA(-IR) has been widely applied in epidemiological studies and in experimental research. HOMA(-IR) denotes a value which represents an estimation for insulin resistance, derived from dividing Insulin and Glucose levels in the blood of a person. The HOMA(-IR) value can be calculated by the following equation:

$$H = \frac{Glucose \times Insulin}{405}$$

wherein H is the HOMA(-IR) value expressed in mg/dL, Glucose represents fasting glucose levels in the blood expressed in mmol/L, Insulin represents fasting insulin levels in the blood expressed in mIU/L. IU (relating to enzyme activity) is an abbreviation of International Units, also called enzyme units. The skilled person in the art is familiar with the methods used to quantify these levels.

Enzyme activity is the amount of substrate converted per unit of time. One IU equals the conversion of one μmol of substrate per minute. For an individual with normal insulin sensitivity, HOMA(-IR) may equal 1. The upper limit of normal HOMA(-IR) is frequently considered to be 2.0, although the normal HOMA(-IR) may be dependent on the characteristics of the population subgroup. In the current disclosure, a healthy subject is considered to have a HOMA-IR value below 2.0 mg/dl, preferably a HOMA-IR value below 1.9, 1.8, or 1.7 mg/dL, more preferably a HOMA-IR value below 1.6, 1.5, 1.4, 1.3, 1.2, 1.1 mg/dL, and most preferred a HOMA-IR value below 1.0. In the current disclosure, a fasting serum insulin level greater than 25 mU/L or 174 pmol/L is considered as indicating insulin resistance.

Other methods may also be suitable to measure insulin resistance. In an embodiment, insulin sensitivity or resistance is measured with the "insulin-suppression test" (IST). In an embodiment, insulin sensitivity or resistance is measured with the "minimal model analysis of frequently sampled intravenous glucose tolerance test" (FSIVGTT). In an embodiment, insulin sensitivity or resistance is measured with the "oral glucose tolerance test" (OGTT).

In a preferred embodiment, the "risk factor for hyperglycemia" as disclosed herein is metabolic syndrome. The term 'metabolic syndrome' as used herein encompasses all conditions diagnosed as "metabolic syndrome" by a professional medical practitioner. In an embodiment, metabolic syndrome may be diagnosed if a subject has at least two, or at least three of the following traits:

Large waist—A waistline that measures at least 35 inches (89 centimeters) for women and 40 inches (102 centimeters) for men;

High triglyceride level—150 milligrams per deciliter (mg/dL), or 1.7 millimoles per liter (mmol/L), or higher of this type of fat found in blood;

Reduced "good" or HDL cholesterol—Less than 40 mg/dl (1.04 mmol/L) in men or less than 50 mg/dL (1.3 mmol/L) in women of high-density lipoprotein (HDL) cholesterol;

Increased blood pressure—130/85 millimeters of mercury (mm Hg) or higher;

Elevated fasting blood sugar—100 mg/dL (5.6 mmol/L) or higher.

In a preferred embodiment, the risk factor for hyperglycemia as disclosed herein is type 2 diabetes. The term "type 2 diabetes" may herein be used interchangeably with "type 2 diabetes mellitus". In the context of the current invention, patients with type 2 diabetes mellitus are preferably characterized by high blood sugar, insulin resistance, and relative lack of insulin.

In a preferred embodiment, the risk factor for hyperglycemia as disclosed herein is obesity.

In a preferred embodiment, the risk factor for hyperglycemia as disclosed herein is being overweight.

As used herein, the term "obesity" means a medical condition in which excess body fat has accumulated to the extent that it may have an adverse effect on health. In some cases, obesity is only a cosmetic concern (requiring non-therapeutic treatment). The professional medical practitioner may establish by one or more means whether a person is obese.

Generally, a body mass index (BMI) of 30.0 or higher is considered to indicate the presence of obesity. In the current disclosure, a BMI of 25.0 to <30 indicates a person being overweight. "Overweight" as used herein refers to a non-medical condition characterized by excess accumulation of body fat.

The present inventors discovered that the hydrolyzed collagen of the invention may have one or more the following actions, e.g. as mechanism-of-action in lowering blood glucose and/or ameliorating hyperglycemia:

increasing the level of one or more incretins in the body, such as by increasing secretion of one or more incretins by gastrointestinal cells;

decreasing the level of one or more inhibitors of incretins (e.g. DPP-IV) in the body, such as by decreasing secretion of one or more inhibitors of incretins by gastrointestinal cells;

increasing blood GLP-1, such as by increasing secretion of GLP-1 by gastrointestinal cells;

decreasing blood glucagon, such as by decreasing secretion of glucagon by pancreatic (alpha) cells;

increasing blood insulin, such as by increasing secretion of insulin by pancreatic (beta) cells;

decreasing the absorption of glucose in the small intestine; and increasing the blood insulin/glucose ratio.

In a preferred embodiment, the hydrolyzed collagen as disclosed herein is for (further) use in one or more selected from the group consisting of:

ameliorating blood GLP-1, preferably increasing blood GLP-1;

ameliorating blood glucagon, preferably deceasing blood glucagon;

ameliorating blood insulin, preferably increasing blood insulin;

ameliorating blood insulin/glucose ratio, preferably increasing blood insulin/glucose ratio;

ameliorating the level of DPP-IV in the body, preferably decreasing the level of DPP-IV in the body, such as by decreasing the secretion of DPP-IV 4 by gastrointestinal cells;

ameliorating the level of one or more incretins in the body, preferably increasing the level of the one or more incretins in the blood, such as by increasing the secretion of the one or more incretins by gastrointestinal cells;

ameliorating glucose absorption in the small intestines, preferably decreasing the absorption of glucose in the small intestines.

The present inventors found that the hydrolyzed collagen of the invention has a particularly high ability to stimulate GLP-1 secretion and/or lower blood glucose. The biological activity appears related to the specific molecular weight and/or molecular weight distribution of the hydrolyzed collagen as obtainable by hydrolysis with the specific combination of enzymes.

In a preferred embodiment, the hydrolyzed collagen is capable of stimulating GLP-1 secretion. The capability of stimulating GLP-1 secretion is preferably in STC-1 cells. The capability of stimulating GLP-1 secretion is preferably demonstrated using the following protocol:

subjecting gelatin to hydrolysis to obtain a hydrolyzed collagen formulation;

subjecting the hydrolyzed collagen formulation to simulated gastrointestinal digestion (SGID) to obtain digested hydrolyzed collagen, preferably according to the protocol described by Song et al. (Food Funct. 2020 Jun. 24; 11(6):5553-5564);

stimulating cells (e.g. STC-1 cells) with the digested hydrolyzed collagen or with a blank as reference, preferably according to the protocol described by Qi et al. (Bio Protoc. 2020 Aug. 20; 10(16): e3717). The cells are preferably stimulated at a concentration in the range of 1-20 mg/ml, preferably at 10 mg/ml;

supernatants are collected 1-3 h after start of the stimulation and GLP-1 levels are determined in the supernatant, for instance by enzyme immunoassay.

A particularly suitable protocol is the protocol described for stimulation of STC-1 cells in Example 1 of the current disclosure.

The capability of stimulating GLP-1 secretion is preferably defined according to an at least 100-fold increase, preferably 500-fold increase, more preferably 1000-fold increase, even more preferably 2000-fold increase, most preferably 5000-fold increase in GLP-1 level after stimulation, preferably relative to the stimulation with a blank reference group (control group).

Hydrolyzed Collagen

As used herein, "hydrolyzed collagen" is a mix of short chains of amino acids derived from a collagen-containing starting material having native (full-length) collagen, generally via hydrolysis steps, including enzymatic hydrolysis (also called enzymatic hydrolyzation). The degree of hydrolysis usually has an impact on the average molecular weight of the final product. Hydrolyzed collagen typically has a molecular weight of 1-10 kDa. The hydrolyzed collagen as taught in the current invention may comprise collagen which is hydrolyzed or partially hydrolyzed. The term "collagen hydrolysate" may be used interchangeably and synonymous with the terms "hydrolyzed collagen" or "collagen peptide".

The hydrolyzed collagen can either be produced from a collagen-containing starting material (such as a connective tissue of an animal) in a one-step process or via the intermediate gelatin stage, in which type A and/or type B gelatin can be used. The hydrolyzed collagen as used herein may thus refer to hydrolyzed gelatin, which is obtained by hydrolysis of gelatin obtained from collagen. The terms "hydrolyzed collagen" and "hydrolyzed gelatin" may be used interchangeably in the current disclosure. The hydrolyzed gelatin is preferably obtained by enzymatic or chemical hydrolysis of gelatin. The hydrolyzed gelatin may be obtained from Type A gelatin, Type B gelatin, or a mixture thereof. The term "hydrolyzed collagen" may be used interchangeably and synonymous with the term "hydrolyzed gelatin".

In a preferred embodiment, the collagen-containing material is gelatin.

The collagen herein may be one or more selected from the group consisting of type I collagen, type II collagen, type III collagen, type V collagen and type X collagen.

Preferably, the hydrolyzed collagen as disclosed herein is derived from one or more types of collagen selected from the group consisting of type I collagen, type II collagen, and type III collagen. In addition or alternatively, the hydrolyzed collagen as disclosed herein is preferably derived from animal raw material that comprises different collagen types, such as two or more of collagen type I, collagen type II, and collagen type III. In addition or alternatively, the hydrolyzed collagen as disclosed herein may be a mixture comprising two or more of type I, type II, and type III collagen.

The hydrolyzed collagen as disclosed herein is preferably derived from collagen type I and/or collagen type II.

The collagen as disclosed herein may be derived from any one or more animals or species of animals, such as bovine species, pig species, and fish species. An "animal" herein may refer to any animal capable of providing connective tissue, of which the connective tissue can be used to prepare hydrolyzed collagen.

In an embodiment, the collagen as taught herein is derived from a cow. In an embodiment, the collagen as taught herein is derived from a pig. In an embodiment, the collagen as taught herein is derived from a fish.

In various embodiments, the collagen as disclosed herein is a mixture of collagen from different sources, such as collagen originating from multiple animal species, and/or collagen originating from different tissues. For example, the collagen as disclosed herein may be a mixture of two or more collagens chosen from the group consisting of fish collagen, porcine collagen, and bovine collagen. In addition or alternatively, the collagen may be a mixture of collagen chosen from skin-, cartilage-, bone-, and/or connective tissue-derived collagen. The term "hide" as used herein means the outer covering of large animals such as from the bovine group or any other large animals. The term "skin" as used herein means the outer covering of small animals like deer, goat, sheep, etc. The terms "skin" and "hide" may herein be used interchangeably, and may refer the outer coverage of an animal, irrespective of size. The "connective tissue" as disclosed herein can be one or more types chosen form the group consisting of connective tissue from the corpus callosum, skin, antler, protrusions (e.g. humps) horns, head, brain, neck, ear, eye, nose, tongue, lip, mouth, esophagus, trachea, limbs, feet, toes, palms, claws, bones, cartilage, bone marrow, joints, membranes, hind, ligaments, tendon, rib, diaphragm, muscle, skeletal muscle, smooth muscle, intestine, blood vessels, bladder, stomach, aorta, heart, liver, kidney, chest, lung, spleen, pancreas, egg, sperm, testis, ovary, nerve, gallbladder, and belly.

In an embodiment, the collagen as taught herein is derived from the skin and/or skin connective tissue. In a preferred embodiment, the collagen as taught herein is derived from cartilage. In a preferred embodiment, the collagen as taught herein is derived from bone. The collagen as disclosed herein may be a mixture of two or more collagens selected from the group consisting of skin collagen, cartilage collagen, and bone collagen.

In a preferred embodiment, the collagen as disclosed herein is derived from one or more tissues selected from the group consisting of skin, scale, cartilage, bone, tendon, ligament, and connective tissue.

In a preferred embodiment, the collagen as disclosed herein is one or more types selected from the group consisting of porcine collagen, bovine collagen, and fish collagen.

Enzymatic Hydrolysis

In an embodiment, the current invention relates to a method for obtaining hydrolyzed collagen, comprising a) providing a collagen-containing material in a liquid formulation; and b) subjecting the collagen-containing material to a combination of enzymes, preferably comprising two or more enzymes selected from the group consisting of a neutral protease, a carboxypeptidase, and an aminopeptidase.

In a preferred embodiment, the current invention relates to a method for obtaining hydrolyzed collagen, comprising a) providing a collagen-containing material in a liquid formulation; and b) subjecting the collagen-containing material to a combination of enzymes comprising a neutral protease, a carboxypeptidase, and an aminopeptidase.

Preferably, step b) of the method as disclosed herein is, or encompasses, a step of enzymatic hydrolysis.

As used herein, the "liquid formulation" is a formulation wherein a collagen-containing material is at least in part dissolvable. In addition or alternatively, the "liquid formulation" is a formulation wherein a collagen-containing material remains at least in part dissolvable after subjecting to a dissolving step. The liquid formulation as disclosed herein is preferably an aqueous formulation. In a preferred embodiment, the liquid formulation as disclosed herein is or comprises water, more preferably the liquid formation is or comprises distilled water and/or demineralized water.

As part of the method as disclosed herein, the collagen-containing material may be provided in the liquid formulation in an amount of at least 10, 15, 20, 25, 30, 35, 40, 45, 50, 55, 60, or 65 wt. % (weight %). In addition or alternatively, the collagen-containing material may be provided in the liquid formulation in an amount of no more than 60, 55, 50, 45, 40, 35, 30, 25, 20, 15, or 10 wt. %.

In an embodiment, the collagen-containing material is provided in the liquid formulation as disclosed herein in an amount of 20-50 wt. %, preferably 30-40 wt. %.

In an embodiment, the combination of enzymes as disclosed herein is a mixture of said enzymes.

In an embodiment, the combination of enzymes as disclosed herein comprises one or more enzymes selected from the group consisting of a neutral protease, a carboxypeptidase, and an aminopeptidase.

In an embodiment, the combination of enzymes as disclosed herein comprises two or more enzymes selected from the group consisting of a neutral protease, a carboxypeptidase, and an aminopeptidase.

In an embodiment, the combination of enzymes as disclosed herein comprises a neutral protease, a carboxypeptidase, and an aminopeptidase.

In an embodiment, the combination of enzymes as disclosed herein comprises a neutral protease and a carboxypeptidase. In an embodiment, the combination of enzymes as disclosed herein comprises a neutral protease and an aminopeptidase. In an embodiment, the combination of enzymes as disclosed herein comprises a carboxypeptidase and an aminopeptidase.

In a preferred embodiment, the combination of enzymes as disclosed herein comprises a neutral protease and one or both of a carboxypeptidase an aminopeptidase.

The term "neutral protease" as used herein means a class of proteases that can act in catalysis in a neutral, weakly acidic, or weakly alkaline environment to catalyze the hydrolysis of peptide bonds of proteins. In the current disclosure, the optimal pH for a neutral protease in enzymatic hydrolysis is considered to be between 6.0 and 7.5. Neutral proteases can be divided into four major categories depending on the catalytic mechanism and the functional group of the active site: serine protease, aspartic protease, cysteine protease, and metalloprotease.

As used herein, a "serine protease" means an enzyme that cleaves peptide bonds in proteins or peptides, wherein serine serves as the nucleophilic amino acid at the active site. The serine protease as disclosed herein may be a chymotrypsin-like (trypsin-like) serine protease.

In addition or alternatively, the serine protease as disclosed herein may be a subtilisin-like serine protease.

As used herein, an "aspartic protease" means a catalytic type of protease enzymes that uses an activated water molecule bound to one or more aspartate residues for catalysis of a protein or a peptide.

As used herein, a "cysteine protease" means a protease with a catalytic mechanism that involves a nucleophilic cysteine thiol in a catalytic triad or dyad for catalysis of a protein or a peptide. "Cysteine proteases" may herein be used interchangeably with "thiol proteases".

As used herein, a "metalloprotease" means a protease for which the catalytic mechanism involves a metal such as zinc or cobalt. In the current disclose, the metalloprotease is preferably a zinc-dependent protease.

The term "carboxypeptidase" as used herein means a protease enzyme that hydrolyzes a peptide bond at the carboxy-terminal (C-terminal) end of a protein or peptide.

Carboxypeptidases are typically classified into one of several families based on their active site mechanism. In an embodiment, the carboxypeptidase herein is a metallocarboxypeptidase, i.e. a carboxypeptidase that uses a metal in the active site for the catalytic mechanism.

The term "aminopeptidase" as used herein means a protease enzyme which cleaves peptide bonds at the N-terminus of a protein or peptide. In the current disclosure, the aminopeptidase is preferably a leucine aminopeptidase. The term "leucine aminopeptidase" as used herein means an aminopeptidase that preferentially catalyzes the hydrolysis of leucine residues at the N-terminus of peptides and proteins.

In a preferred embodiment, the neutral protease as disclosed herein is a serine protease. In a preferred embodiment, the neutral protease as disclosed herein is an aspartic protease. In a preferred embodiment, the neutral protease as disclosed herein is a cysteine protease. In a preferred embodiment, the neutral protease as disclosed herein is a metalloprotease. In a preferred embodiment, the aminopeptidase as disclosed herein is a leucine aminopeptidase.

The "enzyme" in the context of the current invention may be a commercially-available enzyme. In an embodiment, the combination of enzymes as disclosed herein is a commercially available mixture of enzymes. In an embodiment, the combination of enzymes as disclosed herein is commercially obtainable as "Sumizyme", preferably "Sumizyme FP-G".

In an embodiment, the enzyme (e.g. one or more enzymes in the combination of enzymes) as disclosed herein is derived from a microorganism.

In an embodiment, the enzyme (e.g. one or more enzymes in the combination of enzymes) as disclosed herein is derived from a microorganism of the *Aspergillus* genus, preferably from *Aspergillus oryzae* and/or *Aspergillus melleus*.

In an embodiment, the enzyme (e.g. one or more enzymes in the combination of enzymes) as disclosed herein is derived from a microorganism of the *Bacillus* genus (e.g. *Bacillus subtilis*, *Bacillus licheniformis*, *Bacillus amyloliquefaciens*).

In an embodiment, a combination of enzymes is used which comprises no more than one enzyme derived from *Bacillus* sp., thereby excluding blends of endo-proteases from *Bacillus* sp. such as the commercially available as Protamex.

In an embodiment, the enzyme (e.g. one or more enzymes in the combination of enzymes) as disclosed herein is derived from a lactic acid bacteria, preferably one or more genera selected form the group consisting of: *Lactobacillus, Leuconostoc, Pediococcus, Lactococcus*, and *Streptococcus, Aerococcus, Carnobacterium, Enterococcus, Oenococcus, Sporolactobacillus, Tetragenococcus, Vagococcus*, and *Weissella*.

In an embodiment, one or more of the neutral protease, carboxypeptidase, and aminopeptidase are derived from a microorganism of the *Aspergillus* genus, preferably from *Aspergillus oryzae*. In a preferred embodiment, the neutral protease, carboxypeptidase, and aminopeptidase are derived from a microorganism of the *Aspergillus* genus, preferably from *Aspergillus oryzae*.

The proteases used in the invention can be either a mixture of enzymes (e.g. a commercial mixture obtainable from Sumizyme comprising enzymes form *Aspergillus oryzae*), or the proteases may be derived from separate sources (e.g. from different microorganisms or strains therefrom). For example, a neutral protease can be derived from the genus *Bacillus*, the carboxypeptidase from the genus from *Aspergillus*, and the aminopeptidase from the genus *Lactobacillus*.

In an embodiment, the enzyme (e.g. one or more enzymes in the combination of enzymes) as disclosed herein is not derived from a plant (e.g. bromelain, papain).

In a preferred embodiment, the amount of neutral protease used in the enzymatic hydrolysis, preferably in step b) of the method as disclosed herein, is defined by an enzyme activity of 0.2-25000 U/g, preferably 2-2500 U/g, more preferably 20-250 U/g, wherein the weight in g is the total weight of the collagen-containing material and the liquid formulation.

In a preferred embodiment, the amount of carboxypeptidase used in enzymatic hydrolysis, preferably in step b) of the method as disclosed herein, is defined by an enzyme activity of 0.001-500 U/g, preferably 0.01-50 U/g, more preferably 0.1-5 U/g, wherein the weight in g is the total weight of the collagen-containing material and the liquid formulation.

In a preferred embodiment, the amount of aminopeptidase used in enzymatic hydrolysis, preferably in step b) of the method as disclosed herein, is defined by an enzyme activity of 0.002-500 U/g, preferably 0.02-50 U/g, more preferably 0.2-5 U/g, wherein the weight in g is the total weight of the collagen-containing material and the liquid formulation.

The time during which the collagen-containing material is subjected (e.g. in step b of the method) to an enzyme as disclosed herein, preferably one or more of the combination of enzymes as disclosed herein, may be least 10, 20, 30, 40, 50, 60, 70, 80, 90, 100, 110, 120, 130, 140, 150, 160, 170, 180, 190, 200, 210, 220, 230, 240, 300, or 360 min. In addition or alternatively, the time the collagen-containing material is subjected (e.g. in step b of the method) to an enzyme as disclosed herein, preferably one or more of the combination of enzymes as disclosed herein, may be no more than 360, 300, 240, 230, 220, 210, 200, 190, 180, 170, 160, 150, 140, 130, 120, 110, 90, 80, 70, 60, 50, 40, 30, 20, or 10 min.

In a preferred embodiment, the collagen-containing material is subjected (e.g. in step b of the method) to an enzyme as disclosed herein, preferably one or more of the combination of enzymes as disclosed herein, for 60-180 min.

The temperature at which the collagen-containing material is subjected (e.g. in step b of the method) to an enzyme as disclosed herein, preferably one or more of the combination of enzymes as disclosed herein, may be least 15° C., 20° C., 25° C., 30° C., 35° C., 40° C., 45° C., 50° C., 55° C., 60° C., 65° C., 70° C., 75° C., or 80° C. In addition or alternatively, the temperature at which the collagen-containing material is subjected (e.g. in step b of the method) to an enzyme as disclosed herein, preferably one or more of the combination of enzymes as disclosed herein, may be no more than 80° C., 75° C., 70° C., 65° C., 60° C., 55° C., 50° C., 45° C., 40° C., 35° C., 30° C., 25° C., 20° C., or 15° C.

The "temperature" as used herein preferably means the temperature of a liquid formulation wherein a collagen-containing material is comprised, preferably wherein a collagen-containing material is dissolved.

In a preferred embodiment, the collagen-containing material is subjected (e.g. in step b of the method) to an enzyme as disclosed herein, preferably one or more of the combination of enzymes as disclosed herein, at a temperature of 30-60° C.

The use of the term "combination of enzymes" as disclosed herein does not exclude that the collagen-containing material is subjected to enzymes (part of the combination of enzymes) in a sequential fashion. This means that the collagen-containing material is not necessarily subjected to all enzymes of the combination of enzymes at the same time. In an embodiment, the enzymatic hydrolysis as disclosed herein (e.g. in step b of the method) comprises two or more sequential hydrolysis steps, wherein the collagen-containing material is preferably subjected to different enzymes and/or different enzyme mixtures.

In a preferred embodiment, the collagen-containing material is subjected successively to two enzymes in the combination of enzymes, preferably successively to two selected from the neutral protease, the carboxypeptidase and the aminopeptidase.

In an embodiment, the enzymatic hydrolysis, preferably in step b of the method as disclosed herein, involves two or more hydrolysis steps, preferably two steps, wherein:

the collagen-containing material is subjected to the neutral protease in one step, and to the carboxypeptidase and/or the aminopeptidase in another step;

the collagen-containing material is subjected to the carboxypeptidase in one step, and to the neutral protease and/or the aminopeptidase in another step.

the collagen-containing material is subjected to the aminopeptidase in one step, and to the neutral protease and/or the carboxypeptidase in another step.

In an embodiment, the enzymatic hydrolysis as disclosed herein comprises three hydrolysis steps, wherein the collagen-containing material is preferably subjected to the neutral protease, the carboxypeptidase, and the aminopeptidase independently in each of the three hydrolysis steps.

In a preferred embodiment, the collagen-containing material is subjected to all enzymes (of the combination of enzymes disclosed herein) at the same time.

In preferred embodiment, the collagen-containing material is subjected to a mixture comprising two or more of the neutral protease, the carboxypeptidase, and the aminopeptidase, preferably comprising all three of the neutral protease, the carboxypeptidase and the aminopeptidase, wherein the collagen-containing material is more preferably subjected to the mixture for 60-180 min, at 30-60° C., and at pH 5-8.

If there are two or more hydrolysis steps, the "time" the hydrolyzed collagen is subjected to an enzyme preferably means the total time. For example, if hydrolyzed collagen is subjected to enzyme A for 60 min in a first hydrolysis step, and subjected to enzyme A for 60 min in a second hydrolysis step, then it is herein considered that the hydrolyzed collagen is subjected to enzyme A for 120 min.

Product Obtainable by Enzymatic Hydrolysis.

In an aspect, the current invention relates to a hydrolyzed collagen obtainable by the method as disclosed herein.

In the current disclosure, the "hydrolyzed collagen" preferably means the hydrolyzed collagen obtainable by the method as disclosed herein.

In a preferred embodiment, the hydrolyzed collagen disclosed herein, e.g. as obtainable by the method as taught herein, is derived from a collagen-containing material derived from one or more tissues selected from the group consisting of skin, scale, cartilage, bone, tendon, ligament, and connective tissue.

In a preferred embodiment, the hydrolyzed collagen as disclosed herein, e.g. as obtainable by the method as taught herein, is derived from a collagen-containing material wherein the collagen is one or more types selected from the group consisting of porcine collagen, bovine collagen, and fish collagen.

In a preferred embodiment, the hydrolyzed collagen as disclosed herein, e.g. as obtainable by the method as taught herein, is derived from a collagen-containing material, wherein the collagen-containing material is gelatin.

The hydrolyzed collagen as disclosed herein, e.g. as obtainable by the method as taught herein, preferably has a (weight average) molecular weight of 1000-7000 Da. This molecular weight appears to play a role in the high glucose-lowering effect of the collagen hydrolyzed of the invention.

The hydrolyzed collagen, e.g. as obtainable by the method as taught herein, may have a (weight average) molecular weight of at least 1000 Da (e.g. at least 1200 Da, 1400 Da, 1600 Da, or 1800 Da), or at least 1500 Da, or at least 2000 Da, or at least 2500 Da, or at least 3000 Da, or at least 3500 Da, or at least 4000 Da, or at least 4500 Da, or at least 5000 Da, or at least 6000 Da, or at least 6500 Da, or at least 7000 Da. In addition or alternatively, the hydrolyzed collagen, e.g. as obtainable by the method as taught herein, may have a (weight average) molecular weight of no more than 7000 Da, or no more than 6500 Da, or no more than 6000 Da, or no more than 5500 Da, or no more than 5000 Da, or no more than 4500 Da, or no more than 4000 Da, or no more than 3500 Da, or no more than 3000 Da, or no more than 2500 Da, or no more than 2000 Da, or no more than 1500 Da, or no more than 1000 Da.

The average molecular weight as disclosed herein is preferably the weight-average molecular weight.

It appears that the molecular weight plays a role in the ability of the hydrolyzed collagen of the invention to stimulate GLP-1 secretion and/or lower blood glucose.

In an embodiment, the hydrolyzed collagen has a weight-average molecular weight of 1500-4500 Da, preferably 2000-4000 Da, more preferably 2500-3500 Da, even more preferably 2750-3250 Da.

In an embodiment, the hydrolyzed collagen has a number-average ($M_n$) molecular weight of 500-3500 Da, preferably 1000-3000 Da, more preferably 1500-2500 Da, even more preferably 1750-2250 Da.

In an embodiment, the hydrolyzed collagen has a weight-average molecular weight of 2000-4000 Da, preferably 2500-3500 Da, and a number-average molecular weight of 1000-3000 Da, preferably 1500-2500 Da.

In addition or alternatively, it appears that the molecular weight distribution plays a role in the ability of the hydro-lyzed collagen of the invention to stimulate GLP-1 secretion and/or lower blood glucose. In comparison to other hydro-lyzed collagens—e.g., which are not obtained by enzymatic hydrolysis with a combination of enzymes comprising two or more enzymes selected from the group consisting of a neutral protease, a carboxypeptidase, and an aminopepti-dase—the hydrolyzed collagen of the invention in particular may have:

a relatively high fraction of collagen peptides which fall in the range of 2000-5000 Da (e.g. at least 35%, or at least 40%, or even at least 45%); and/or a relatively low fraction of collagen peptides which fall in the range of below 1000 Da (e.g. no more than 15%, or no more than 12%, or even no more than 10%); and/or a relatively low fraction of collagen peptides which fall in the range of above 10000 Da (e.g. no more than 5%, or no more than 2%, or even no more than 1%).

In a preferred embodiment, the hydrolyzed collagen com-prises 1-20%, preferably 2-12% by weight of collagen peptides with a molecular weight below 1000 Da, calculated on total weight of collagen peptides in the hydrolyzed collagen.

In a preferred embodiment, the hydrolyzed collagen com-prises 20-40%, preferably 25-35% by weight of collagen peptides with a molecular weight in the range of 1000-2000 Da, calculated on total weight of collagen peptides in the hydrolyzed collagen.

Preferably, the hydrolyzed collagen comprises less than 35%, more preferably less than 32.5%, even more more preferably less than 30% by weight of collagen peptides with a molecular weight in the range of 1000-2000 Da, calculated on total weight of collagen peptides in the hydro-lyzed collagen.

In a preferred embodiment, the hydrolyzed collagen com-prises 35-60%, preferably 40-55% by weight of collagen peptides with a molecular weight in the range of 2000-5000 Da, calculated on total weight of collagen peptides in the hydrolyzed collagen.

Preferably, the hydrolyzed collagen comprises more than 40%, more preferably more than 42.5%, even more prefer-ably more than 45% by weight of collagen peptides with a molecular weight in the range of 2000-5000 Da, calculated on total weight of collagen peptides in the hydrolyzed collagen.

In a preferred embodiment, the hydrolyzed collagen com-prises 5-25%, preferably 10-20% by weight of collagen peptides with a molecular weight in the range of 5000-10000 Da, calculated on total weight of collagen peptides in the hydrolyzed collagen.

In a preferred embodiment, the hydrolyzed collagen com-prises 0-10%, preferably 0.1-5%, more preferably 0.2-2% by weight of collagen peptides with a molecular weight above 10000 Da, calculated on total weight of collagen peptides in the hydrolyzed collagen.

A preferred way of measuring the molecular weight and molecular weight distribution of hydrolyzed collagen is by high performance size exclusion chromatography (HPSEC). The following protocol is a preferred HPSEC protocol:

The Agilent HPLC, 1260 Infinity series (G1316A, G1329B, G1311C, G1315D) with a TSKgel SWXL precol-umn und a G2000SWXL column (Tosoh Bioscience) is used. Analysis is performed with the WinGPC software (PSS). The eluent is 100 mM phosphate buffer pH 5.3. Samples are eluted from the column (e.g. 0.5 mL/min, isocratic) and monitored with UV detection (e.g. 214 nm, analysis time: 40 min per injection+180 min equilibration). Calibration is performed with the Narrow Calibration Stan-dard (Low FILK).

The hydrolyzed collagen, e.g. as obtainable by the method as taught herein, preferably has a polydispersity of 1.2-1.8, more preferably 1.3-1.7, even more preferably 1.4-1.6. This polydispersity appears to play a role in the high glucose-lowering effect of the collagen hydrolyzed of the invention.

The polydispersity of the hydrolyzed collagen may be no more than 1.85, or no more than 1.75, or no more than 1.70, or no more than 1.65, or no more than 1.60, or no more than 1.55. In addition or alternatively, the polydispersity of the hydrolyzed collagen may be at least 1.20, or at least 1.25, or at least 1.30, or at least 1.35, or at least 1.40, or at least 1.45, or at least 1.50, or at least 1.55.

The "polydispersity" as used herein means $M_w/M_n$, where $M_w$ is the weight-average molecular weight (Da) and $M_n$ is the number-average molecular weight (Da).

$M_w$ is given by the following equation:

$$M_w = \frac{\sum_i N_i M_i^2}{\sum_i N_i M_i}$$

$M_n$ is given by the following equation:

$$M_n = \frac{\sum_i N_i M_i}{\sum_i N_i}$$

Where $N_i$ is the number of molecules with weight $M_i$.

Administration of Hydrolyzed Collagen

In a preferred embodiment, the hydrolyzed collagen as disclosed herein is administered orally.

To ameliorate the postprandial glucose levels, the hydrolyzed collagen as disclosed herein is preferably administered during or around a meal. In the context of the current invention, the hydrolyzed collagen is preferably administered no more than 240, 180, 120, 60, 30, or 15 min separated (before or after) from a meal. In a preferred embodiment, the hydrolyzed collagen as disclosed herein is administered no more than 60 min separated (before or after) from a meal.

In different embodiments, the daily dose of the hydrolyzed collagen as disclosed herein is at least 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, or 200, all in g, wherein the daily dose is the total dry weight amount administered to a subject per day. In addition or alternatively, in different embodiments, the daily dose of the hydrolyzed collagen as disclosed herein is no more than 200, 190, 180, 170, 160, 150, 140, 130, 120, 110, 100, 95, 90, 85, 80, 75, 70, 65, 60, 55, 50, 45, 40, 35, 30, 25, 20, 15, 10, 5, or 1, all in g, wherein the daily dose is the total dry weight amount administered to a subject per day.

In a preferred embodiment, the use of hydrolyzed collagen as disclosed herein comprises administering the hydrolyzed collagen in an amount of between 1 g and 200 g, or between 1 g and 100 g, or between 2 g and 50 g, or between 5 g and 25 g, wherein the daily dose is the total dry weight amount administered to a subject per day.

In a preferred embodiment, the use of hydrolyzed collagen as disclosed herein comprises administering the hydrolyzed collagen at a daily dose in an amount of 1-100 g, preferably 2-50 g, more preferably 5-25 g, wherein the amount is the dry weight amount of hydrolyzed collagen.

In different embodiments, the unit dose of hydrolyzed collagen as disclosed herein is in an amount of at least 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 130, 140, 150, 160, 170, 180, 190, or 200, all in g, wherein the amount is the dry weight amount of hydrolyzed collagen. In addition or alternatively, in different embodiments, the unit dose of hydrolyzed collagen as disclosed herein is in an amount of no more than 200, 190, 180, 170, 160, 150, 140, 130, 120, 110, 100, 95, 90, 85, 80, 75, 70, 65, 60, 55, 50, 45, 40, 35, 30, 25, 20, 15, 14, 13, 12, 11, 10, 9, 8, 7, 6, 5, 4, 3, 2, or 1, all in g, wherein the amount is the dry weight amount of hydrolyzed collagen.

In an embodiment, the hydrolyzed collagen as disclosed herein is administered in a unit dose in an amount of between 0.5 g and 200 g, or between 1 g and 100 g, or between 2 g and 50 g, or between 5 g and 25 g, or between 5 and 15 g, wherein the amount is the dry weight amount of hydrolyzed collagen.

In an embodiment, the use of hydrolyzed collagen as disclosed herein comprises administering the hydrolyzed collagen at a unit dose in an amount of 2-50 g, preferably 5-25 g, more preferably 5-15 g, wherein the amount is the dry weight amount of hydrolyzed collagen.

The daily dose of hydrolyzed collagen may be administered as a single unit dose, or as two, three, four or more unit doses. The two or more unit doses may be equal or different in amount. The daily dose of hydrolyzed collagen as disclosed herein is preferably administered as two unit doses, more preferably as two unit doses each corresponding to 30-70%, preferably 40-60% of the daily dose amount.

In an embodiment, the two or more unit doses as disclosed herein are administered at least 1, 2, 3, 4, 5, 6, 7, 8, 9, 10, 11, or 12 hours separated from each other.

In a preferred embodiment, the dosage regimen for hydrolyzed collagen as disclosed herein comprises administering the daily dose of hydrolyzed collagen as two unit doses, wherein:

each unit dose is in an amount of 5-25 g, preferably 5-15 g, wherein the amount is the dry weight amount of hydrolyzed collagen; and/or the two unit doses are administered at least 6 hours, preferably 8 hours, more preferably 12 hours separated from each other.

In a preferred embodiment, the daily dose of hydrolyzed collagen is administered as two or more unit doses, wherein:

each unit dose is in an amount of 5-25 g, preferably 5-15 g, wherein the amount is the dry weight amount of hydrolyzed collagen; and/or the two or more unit doses are administered at least 6 hours, preferably 8 hours, more preferably 12 hours separated from each other.

In a preferred embodiment, the hydrolyzed collagen as disclosed herein is administered together with a meal.

In an embodiment, the dosage regimen for hydrolyzed collagen as disclosed herein comprises administering hydrolyzed collagen at least once a week.

In an embodiment, the dosage regimen for hydrolyzed collagen as disclosed herein comprises administering hydrolyzed collagen every day or every other day.

In an embodiment, the hydrolyzed collagen is administered every day or every other day.

In an embodiment, the dosage regimen for hydrolyzed collagen as disclosed herein comprises administering hydrolyzed collagen at least once a day.

In an embodiment, the hydrolyzed collagen is administered at least once a day.

In an embodiment, the dosage regimen for hydrolyzed collagen as disclosed herein comprises administering hydrolyzed collagen for at least 2 consecutive days, preferably for at least 4 consecutive days, more preferably for at least 7 consecutive days.

In an embodiment, the dosage regimen for hydrolyzed collagen as disclosed herein comprises administering hydrolyzed collagen for at least 2 consecutive weeks, preferably for at least 4 consecutive weeks, more preferably for at least 8 consecutive weeks.

In an embodiment, the dosage regimen for hydrolyzed collagen as disclosed herein comprises administering hydrolyzed collagen for at least one week, preferably for at least two consecutive weeks, more preferably for at least four consecutive weeks.

Formulation of Hydrolyzed Collagen

The hydrolyzed collagen as disclosed herein may be provided in a food formulation, feed formulation, food supplement formulation, feed supplement formulation, or pharmaceutical formulation, preferably a food supplement formulation.

The hydrolyzed collagen as disclosed herein may be provided in a solid dosage form such as a capsule, a tablet, or a powder, preferably a powder.

The hydrolyzed collagen as disclosed herein may be provided in a formulation such as a drinkable solution or suspension, drink such as beer, syrup, artificially-flavoured drink, carbonated beverage, (water-soluble) powdered mixture, (water-soluble) paste, (water-soluble) powder, (water-soluble) tablet, (water-soluble) pill, (water-soluble) dragee, (water-soluble) caplet, (water-soluble) sachet, or (water-soluble) capsule. In addition or alternatively, the hydrolyzed collagen as taught herein may be present in a functional food, e.g. a juice, shake, dairy drink, yoghurt, yoghurt drink, dessert, energy bar, nutritional bar, slimming bar, or confectionery such as gummies or center-filled gummies.

Use of Hydrolyzed Collagen in a Method of Treatment

In an embodiment, the current invention relates to a method of treatment, preferably a therapeutic method of treatment, for reducing blood glucose.

In an embodiment, the current invention relates to a method of treatment, preferably a therapeutic method of treatment, for ameliorating hyperglycemia.

In an embodiment, the current invention relates to a method of treatment, preferably a therapeutic method of treatment, for ameliorating a risk factor of hyperglycemia.

The method of treatment as disclosed herein may be used in subjects experiencing high blood sugar (e.g. hyperglycemia), wherein the method of treatment may be preventive in nature. The method of treatment may comprise one or more features of the embodiments described herein for the use of hydrolyzed collagen in reducing blood glucose and/or ameliorating (a risk factor of) hyperglycemia, including the type(s) of hydrolyzed collagen for the use as disclosed herein, the formulation(s) of hydrolyzed collagen for the use as disclosed herein, the timing(s) of hydrolyzed collagen administration or intake for the use as disclosed herein, and the dosing(s) of hydrolyzed collagen administration or intake (e.g. dosage regimens, unit doses, daily doses) for the use as disclosed herein.

Use of Hydrolyzed Collagen for the Manufacture of a Medicament

In an embodiment, the current invention relates to the use of hydrolyzed collagen for the manufacture of a medicament for reducing blood glucose, wherein the hydrolyzed collagen is obtained by enzymatic hydrolysis of a collagen-containing material with a combination of enzymes, preferably comprising two or more enzymes selected from the group consisting of a neutral protease, a carboxypeptidase, and an aminopeptidase.

In an embodiment, the current invention relates to the use of hydrolyzed collagen for the manufacture of a medicament for ameliorating hyperglycemia, wherein the hydrolyzed collagen is obtained by enzymatic hydrolysis of a collagen-containing material with a combination of enzymes, preferably comprising two or more enzymes selected from the group consisting of a neutral protease, a carboxypeptidase, and an aminopeptidase.

In an embodiment, the current invention relates to the use of hydrolyzed collagen for the manufacture of a medicament for ameliorating a risk factor of hyperglycemia, wherein the hydrolyzed collagen is obtained by enzymatic hydrolysis of a collagen-containing material with a combination of enzymes, preferably comprising two or more enzymes selected from the group consisting of a neutral protease, a carboxypeptidase, and an aminopeptidase.

The use of hydrolyzed collagen for the manufacture of a medicament as disclosed herein may comprise one or more features of the embodiments described herein for the use of hydrolyzed collagen in reducing blood glucose and/or ameliorating (a risk factor of) hyperglycemia, including the type(s) of hydrolyzed collagen for the use as disclosed herein, the formulation(s) of hydrolyzed collagen for the use as disclosed herein, the timing(s) of hydrolyzed collagen administration or intake for the use as disclosed herein, and the dosing(s) of hydrolyzed collagen administration or intake (e.g. dosage regimens, unit doses, daily doses daily amounts) for the use as disclosed herein.

General Definitions

The terms 'comprising' or 'to comprise' and their conjugations, as used herein, refer to a situation wherein said terms are used in their non-limiting sense to mean that items following the word are included, but items not specifically mentioned are not excluded. It also encompasses the more limiting verb 'to consist essentially of' and 'to consist of'.

Reference to an element by the indefinite article 'a' or 'an' does not exclude the possibility that more than one of the elements is present, unless the context clearly requires that there be one and only one of the elements. The indefinite article 'a' or 'an' thus usually means 'at least one'.

The terms 'to increase' and 'increased level' and the terms 'to decrease' and 'decreased level' (or to 'reduce" and "reduced level") preferably refer to a change of at least 5%, such as 10%, 15%, 20%, 25%, 30%, 35%, 40%, 45%, 50% higher or lower, respectively, than the corresponding level in a control or reference. In addition or alternatively, a level in a sample may be increased or decreased when it is statistically significantly increased or decreased compared to a level in a control or reference, irrespective of the size of change.

The term "meal" as used herein refers a eating occasion that takes place at a certain time and includes prepared food. Meals occur on a daily basis, typically several times a day. Breakfast, lunch, and dinner are considered to be the main meals. In addition or alternatively, a meal may be considered to comprise reasonably large amount of food (i.e. at least 500-1000 kcal per meal).

As used herein, the terms "subject" or "individual" refer to any animal (e.g. a mammal), including, preferably a human.

The terms "administer" or "administration" as used herein relate to the act of providing an agent to a subject consuming it. A subject consuming a certain agent may administer it to himself/herself/itself. In such a case the terms "administered to" may be interpreted as "taken by", "used by", or "consumed by".

The term "unit dose" as used herein relates to an amount or unit of e.g. a compound, substance, active ingredient or composition to be used at once. The unit dose may for example be in a pre-prepared form (e.g. prepacked dosage) ready for administration. The unit dose may for example (also) be identifiable from the product packaging or label. The total daily dose may be divided into multiple unit doses The term "active ingredient" as used herein means any substance, compound or composition which induces a biological response measurable in vitro and/or in vivo, as opposed to a substance, compound or composition which provides only a physical function. The biological response may be a direct or an indirect response preferably measured in a cell or organ.

CLAUSES

Herein, clauses are embodiments of the invention. Features of clauses (embodiments) herein can be combined.

Clause 1: Hydrolyzed collagen for use in decreasing blood glucose, wherein the hydrolyzed collagen is obtained by enzymatic hydrolysis of a collagen-containing material with a combination of enzymes comprising two or more enzymes selected from the group consisting of a neutral protease, a carboxypeptidase, and an aminopeptidase.

Clause 2: Hydrolyzed collagen for use according to clause 1, wherein the combination of enzymes comprises a neutral protease, a carboxypeptidase, and an aminopeptidase.

Clause 3: Hydrolyzed collagen for use according to clause 1 or 2, for use in ameliorating hyperglycemia.

Clause 4: Hydrolyzed collagen for use according to clause 1 or 2, for use in ameliorating a risk factor for hyperglycemia.

Clause 5: Hydrolyzed collagen for use according to clause 4, wherein the risk factor for hyperglycemia is one or more selected from the group consisting of insulin resistance, type 2 diabetes, gestational diabetes, high body mass index, obesity, and hyperglucagonemia.

Clause 6: Hydrolyzed collagen for use according to any one of the previous clauses, for use in ameliorating postprandial glucose.

Clause 7: Hydrolyzed collagen for use according to any one of the previous clauses, for use in one or more selected from the group consisting of:
increasing blood glucagon-like peptide-1;
decreasing blood glucagon;
increasing blood insulin;
increasing blood insulin/glucose ratio.

Clause 8: Hydrolyzed collagen for use according to any one of the previous clauses, wherein the hydrolyzed collagen is administered at a daily dose in an amount of 1-100 gram, preferably 2-50 g, more preferably 5-25 g, wherein the amount is the dry weight amount.

Clause 9: Hydrolyzed collagen for use according to any one of the previous clauses, wherein the hydrolyzed collagen is administered orally, preferably as a food supplement.

Clause 10: Hydrolyzed collagen for use according to any one of the previous clauses, wherein the hydrolyzed collagen is administered no more than 60 min separated from a meal.

Clause 11: Hydrolyzed collagen for use according to any one of the previous clauses, wherein the collagen-containing material is derived from one or more tissues selected from the group consisting of skin, scale, cartilage, bone, tendon, ligament, and connective tissue.

Clause 12: Hydrolyzed collagen for use according to any one of the previous clauses, wherein the collagen is one or more types selected from the group consisting of porcine collagen, bovine collagen, and fish collagen.

Clause 13: Hydrolyzed collagen for use according to any one of the previous clauses, wherein the collagen-containing material is gelatin.

Clause 14: Hydrolyzed collagen for use according to any one of the previous clauses, wherein the hydrolyzed collagen has an average molecular weight of 1000-7000 Da and/or a polydispersity of 1.2-1.8.

Clause 15: Method for obtaining hydrolyzed collagen, comprising
a) providing a collagen-containing material in a liquid formulation; and
b) subjecting the collagen-containing material to a combination of enzymes comprising two or more enzymes selected from the group consisting of a neutral protease, a carboxypeptidase, and an aminopeptidase.

Clause 16: Method according to clause 15, wherein the combination of enzymes comprises a neutral protease, a carboxypeptidase, and an aminopeptidase.

Clause 17: Method according to clause 15 or 16, wherein the neutral protease is one or more selected from the group consisting of serine protease, aspartic protease, cysteine protease, and metalloprotease.

Clause 18: Method according to any one of clauses 15-17, wherein the aminopeptidase is leucine aminopeptidase.

Clause 19: Method according to any one of clauses 15-18, wherein one or more of the neutral protease, carboxypeptidase, and aminopeptidase are derived from a microorganism of the *Aspergillus* genus, preferably from *Aspergillus oryzae*.

Clause 20: Method according to any one of clauses 15-19, wherein the collagen-containing material is subjected to an amount of neutral protease defined by an enzyme activity of 0.2-25000 U/g, preferably 2-2500 U/g, more preferably 20-250 U/g, wherein the weight in g is the total weight of the collagen-containing material and the liquid formulation.

Clause 21: Method according to any one of clauses 15-20, wherein the collagen-containing material is subjected to an amount of carboxypeptidase defined by an enzyme activity of 0.001-500 U/g, preferably 0.01-50 U/g, more preferably 0.1-5 U/g, wherein the weight in g is the total weight of the collagen-containing material and the liquid formulation.

Clause 22: Method according to any one of clauses 15-21, wherein the collagen-containing material is subjected to an amount of aminopeptidase defined by an enzyme activity of 0.002-500 U/g, preferably 0.02-50 U/g, more preferably 0.2-5 U/g, wherein the weight in g is the total weight of the collagen-containing material and the liquid formulation.

Clause 23: Method according to any one of clauses 15-22, wherein the collagen-containing material is subjected to one or more enzymes in the combination of enzymes for 60-180 min.

Clause 24: Method according to any one of clauses 15-23, wherein the collagen-containing material is subjected to one or more enzymes in the combination of enzymes at 30-60° C.

Clause 25: Method according to any one of clauses 15-24, wherein the collagen-containing material is subjected to one or more enzymes in the combination of enzymes at pH 5-8.

Clause 26: Method according to any one of clauses 15-25, wherein the collagen-containing material is subjected successively to two or more enzymes in the combination of enzymes.

Clause 27: Method according to any one of clauses 15-26, wherein the collagen-containing material is subjected simultaneously to two or more enzymes in the combination of enzymes.

Clause 28: Method according to clause 27, wherein the collagen-containing material is subjected to a mixture comprising the combination of enzymes.

Clause 29: Method according to any one of clauses 15-28, wherein the collagen-containing material is provided in a liquid formulation in an amount of 20-50 wt. %, preferably 30-40 wt. %.

Clause 30: Method according to any one of clauses 15-29, wherein the collagen-containing material is derived from one or more tissues selected from the group consisting of skin, scale, cartilage, bone, tendon, ligament, and connective tissue.

Clause 31: Method according to any one of clauses 15-30, wherein the collagen is one or more types selected from the group consisting of porcine collagen, bovine collagen, and fish collagen.

Clause 32: Method according to any one of clauses 15-31, wherein the collagen-containing material is gelatin.

Clause 33: Hydrolyzed collagen obtainable by the method according to any one of clauses 15-32.

Clause 34: Hydrolyzed collagen according to clause 33, wherein the hydrolyzed collagen has an average molecular weight of 1000-7000 Da and/or a polydispersity of 1.2-1.8.

Clause 35: Hydrolyzed collagen according to clause 33 or 34, for use as defined in any one of clauses 1-14.

Clause 36: Hydrolyzed collagen for use in ameliorating hyperglycemia or a risk factor for hyperglycemia, wherein the hydrolyzed collagen is obtained by enzymatic hydrolysis of a collagen-containing material with a combination of enzymes comprising two or more enzymes selected from the group consisting of a neutral protease, a carboxypeptidase, and an aminopeptidase.

Clause 37: Hydrolyzed collagen for use according to clause 36, wherein the combination of enzymes comprises a neutral protease, a carboxypeptidase, and an aminopeptidase.

Clause 38: Hydrolyzed collagen for use according to clause 36-37, wherein the risk factor for hyperglycemia is one or more selected from the group consisting of insulin resistance, type 2 diabetes, gestational diabetes, high body mass index, obesity, and hyperglucagonemia.

Clause 39: Hydrolyzed collagen for use according to any one of clauses 36-38, for use in one or more selected from the group consisting of:
increasing blood glucagon-like peptide-1;
decreasing blood glucagon;
increasing blood insulin;
increasing blood insulin/glucose ratio.

Clause 40: Hydrolyzed collagen for use according to any one of clauses 36-39, wherein the hydrolyzed collagen is administered at a daily dose in an amount of 1-100 gram, preferably 2-50 g, more preferably 5-25 g, wherein the amount is the dry weight amount.

Clause 41: Hydrolyzed collagen for use according to any one of the clauses 36-41, wherein the hydrolyzed collagen is administered orally, preferably as a food supplement.

Clause 42: Hydrolyzed collagen for use according to any one clauses 36-41, wherein the hydrolyzed collagen is administered no more than 60 min separated from a meal.

Clause 43: Hydrolyzed collagen for use according to any one clauses 36-42, wherein the collagen-containing material is derived from one or more tissues selected from the group consisting of skin, scale, cartilage, bone, tendon, ligament, and connective tissue.

Clause 44: Hydrolyzed collagen for use according to any one of clauses 36-43, wherein the collagen is one or more types selected from the group consisting of porcine collagen, bovine collagen, and fish collagen.

Clause 45: Hydrolyzed collagen for use according to any one of clauses 36-44, wherein the collagen-containing material is gelatin.

Clause 46: Hydrolyzed collagen for use according to any one of clauses 36-45, wherein the hydrolyzed collagen has an average molecular weight of 1000-7000 Da and/or a polydispersity of 1.2-1.8.

Clause 47: Use of hydrolyzed collagen for non-therapeutic lowering of blood glucose, wherein the hydrolyzed collagen is as defined by any one of clauses 1-11.

Clause 48: Use according to clause 47, wherein the use is in ameliorating postprandial glucose.

Clause 49: Use according to clause 47 or 48, wherein the hydrolyzed collagen is administered as defined in any one of clauses 40-42.

Clause 50: Method for obtaining hydrolyzed collagen, comprising
a) providing a collagen-containing material in a liquid formulation; and
b) subjecting the collagen-containing material to a combination of enzymes comprising two or more enzymes selected from the group consisting of a neutral protease, a carboxypeptidase, and an aminopeptidase.

Clause 51: Method according to clause 50, wherein the combination of enzymes comprises a neutral protease, a carboxypeptidase, and an aminopeptidase.

Clause 52: Method according to clause 50 or 51, wherein the neutral protease is one or more selected from the group consisting of serine protease, aspartic protease, cysteine protease, and metalloprotease.

Clause 53: Method according to any one of clauses 50-52, wherein the aminopeptidase is leucine aminopeptidase.

Clause 54: Method according to any one of clauses 50-53, wherein one or more of the neutral protease, carboxypeptidase, and aminopeptidase are derived from a microorganism of the *Aspergillus* genus, preferably from *Aspergillus oryzae*.

Clause 55: Method according to any one of clauses 50-54, wherein the collagen-containing material is subjected to an amount of neutral protease defined by an enzyme activity of 0.2-25000 U/g, preferably 2-2500 U/g, more preferably 20-250 U/g, wherein the weight in g is the total weight of the collagen-containing material and the liquid formulation.

Clause 56: Method according to any one of clauses 50-55, wherein the collagen-containing material is subjected to an amount of carboxypeptidase defined by an enzyme activity of 0.001-500 U/g, preferably 0.01-50 U/g, more preferably 0.1-5 U/g, wherein the weight in g is the total weight of the collagen-containing material and the liquid formulation.

Clause 57: Method according to any one of clauses 50-56, wherein the collagen-containing material is subjected to an amount of carboxypeptidase defined by an enzyme activity of 0.001-500 U/g, preferably 0.01-50 U/g, more preferably 0.1-5 U/g, wherein the weight in g is the total weight of the collagen-containing material and the liquid formulation.

Clause 58: Method according to any one of clauses 50-57, wherein the collagen-containing material is subjected to an amount of aminopeptidase defined by an enzyme activity of 0.002-500 U/g, preferably 0.02-50 U/g, more preferably 0.2-5 U/g, wherein the weight in g is the total weight of the collagen-containing material and the liquid formulation.

Clause 59: Method according to any one of clauses 50-58, wherein the collagen-containing material is subjected to one or more enzymes in the combination of enzymes for 60-180 min.

Clause 60: Method according to any one of clauses 50-59, wherein the collagen-containing material is subjected to one or more enzymes in the combination of enzymes at 30-60° C.

Clause 61: Method according to any one of clauses 50-60, wherein the collagen-containing material is subjected to one or more enzymes in the combination of enzymes at pH 5-8.

Clause 62: Method according to any one of clauses 50-61, wherein the collagen-containing material is subjected successively to two or more enzymes in the combination of enzymes.

Clause 63: Method according to any one of clauses 50-62, wherein the collagen-containing material is subjected simultaneously to two or more enzymes in the combination of enzymes.

Clause 64: Method according to clause 63, wherein the collagen-containing material is subjected to a mixture comprising the combination of enzymes Clause 65: Method according to any one of clauses 50-64 wherein the collagen-containing material is provided in a liquid formulation in an amount of 20-50 wt. %, preferably 30-40 wt. %.

Clause 66: Method according to any one of clauses 50-65, wherein the collagen-containing material is derived from one or more tissues selected from the group consisting of skin, scale, cartilage, bone, tendon, ligament, and connective tissue.

Clause 67: Method according to any one of clauses 50-66, wherein the collagen-containing material is derived from one or more tissues selected from the group consisting of skin, scale, cartilage, bone, tendon, ligament, and connective tissue.

Clause 68: Method according to any one of clauses 50-67, wherein the collagen-containing material is gelatin.

Clause 69: Hydrolyzed collagen obtainable by the method according to any one of clauses 50-68, wherein the hydrolyzed collagen:

has a weight average molecular weight of 2000-4000 Da, preferably 2500-3500 Da; and comprises 35-60% by weight of collagen peptides with a molecular weight in the range of 2000-5000 Da, calculated on total weight of collagen peptides in the hydrolyzed collagen.

Clause 70: Hydrolyzed collagen according to clause 69, wherein the hydrolyzed collagen comprises more than 40% by weight of collagen peptides with a molecular weight in the range of 2000-5000 Da, calculated on total weight of collagen peptides in the hydrolyzed collagen.

Clause 71: Hydrolyzed collagen according to clause 69 or 70, wherein the hydrolyzed collagen comprises:

1-20% by weight of collagen peptides with a molecular weight below 1000 Da; and/or 20-40% by weight of collagen peptides with a molecular weight of 1000-2000 Da; and/or 5-25% by weight of collagen peptides with a molecular weight of 5000-10000 Da; and/or 0-10% by weight of collagen peptides with a molecular weight more than 10000 Da, calculated on the total weight of collagen peptides in the hydrolyzed collagen.

Clause 72: Hydrolyzed collagen according to any one of clauses 69-71, wherein the hydrolyzed collagen has a polydispersity of 1.2-1.8.

Clause 73: Hydrolyzed collagen according to any one of clauses 69-72, wherein the hydrolyzed collagen is capable of stimulating glucagon-like peptide-1 secretion.

Clause 74: Hydrolyzed collagen according to any one of clauses 69-73, for use in ameliorating hyperglycemia or a risk factor of hyperglycemia as defined in any one of clauses 36-46

Clause 75: Use of hydrolyzed collagen according to any one of clauses 69-73 in non-therapeutic lowering of blood glucose as defined in any one clauses 47-49.

FIGURE LEGENDS

FIG. 1. GLP-1 secretion by STC-1 cells following incubation with 10 mg/ml of different hydrolyzed collagen fractions, as obtained by the different enzymatic treatments. Supernatants were collected after 2 h of incubation. GLP-1 levels were determined by enzyme immunoassay. Results are expressed in mean (n=3)±standard deviation. "H080" denotes the hydrolyzed collagen of the invention.

FIG. 2. Area Under the Curve (AUC) of blood glucose levels in mice after glucose load at time 0 and intake of the active ingredient/vehicle at time-45 min. "H080" denotes the hydrolyzed collagen of the invention.

FIG. 3. Ratio of insulin/blood glucose levels in mice at time 15 min, after glucose load at time 0 and intake of the product/drug/vehicle at time-45 min. "H080" denotes the hydrolyzed collagen of the invention.

FIG. 4. Plasma GLP-1 levels in mice after 15 and 30 minutes after intake of H080 hydrolyzed collagen, compared to baseline. "H080" denotes the hydrolyzed collagen of the invention.

FIG. 5. Plasma GIP levels in mice at 15 and 30 minutes after intake of H080 hydrolyzed collagen, compared to baseline. "H080" denotes the hydrolyzed collagen of the invention.

EXPERIMENTAL SECTION

Example 1

Example 1 shows the effect of a gelatin hydrolysate obtained by enzymatic hydrolysis with a combination of enzymes chosen from a neutral protease, a carboxypeptidase and an aminopeptidase on increasing in vitro GLP-1 and lowering in vivo blood glucose.

Study Design

Fourteen different enzyme (mixtures) were used in the hydrolysis of gelatin into hydrolyzed collagen formulations. The hydrolyzed collagen formulations obtained thereby were subjected to simulated gastrointestinal digestion (SGID) to obtain bioactive hydrolyzed collagen fractions as would be expected after in vivo ingestion and digestion (Song et al. Food Funct. 2020 Jun. 24; 11(6):5553-5564).

The hydrolyzed collagen fractions were screened in vitro for their ability to enhance GLP-1 secretion by STC-1 cells. STC-1 cells are an intestinal secretin tumor cells and are reported to be a predictive cell model to study hormonal secretion mechanisms in the gastrointestinal tract (Qi et al. Bio Protoc. 2020 Aug. 20; 10(16): e3717). GLP-1 acts as a main determinant of blood glucose homeostasis, mostly by regulating gastric emptying, enhancing pancreatic insulin secretion, and suppressing pancreatic glucagon secretion. The GLP-1 secretion by STC-1 cells was therefore the preferred outcome parameter determine how the hydrolyzed collagen fractions may ameliorate glucose levels in the body.

The most promising hydrolyzed collagen fraction identified in vitro was further tested for its glucose-lowering activity in mice. The glucose-lowering activity was established based on the changes in plasma GLP-1, GIP, glucose, and insulin. The efficacy of the hydrolyzed collagen fraction was compared to that of the glucose-lowering medicine Sitagliptin.

Methods

Enzymatic Hydrolysis of Collagen

Gelatin powder was dissolved in demi water by heating and stirring to provide a 35 wt. % gelatin solution. The temperature of the gelatin solution was adjusted to 40-55° C. The pH of the gelatin was adjusted to pH 5.5-8.0. When the appropriate temperature and pH was reached, the enzymes (mixtures) as shown in in Table 1 were added and hydrolysis was carried out under stirring. For the "H080" condition, a commercially available enzyme mixture was used (Sumizyme FP-G obtainable from Takabio, Japan), which comprises a mixture of a neutral protease, a carboxypeptidase, and an aminopeptidase, derived from *Aspergillus oryzae*. The temperature was kept constant. After 120 min, enzymatic hydrolysis was terminated by heat inactivation of the enzymes. Subsequently, the solution was cooled down to 55° C. The hydrolyzed gelatin solution was subjected to purification, filtration and sterilization. A final hydrolyzed gelatin powder was obtained by spray drying.

TABLE 1

Overview of enzyme (mixtures) used for hydrolysis of collagen

| Group name | Activity of enzyme(s) | | | |
| --- | --- | --- | --- | --- |
| | Enzym 1 | Enzym 2 | Enzym 3 | Cleavage site |
| Blank | — | — | — | — |
| CH1 | Neutral protease (serine protease) | — | — | Nonterminal amino acids |
| CH2 | Neutral protease (serine protease) | — | — | Nonterminal amino acids |
| CH3 | Neutral protease (serine protease) | Neutral protease (metallo-protease) | — | Nonterminal amino acids |
| CH4 | Neutral protease (Serine protease) | — | — | Nonterminal amino acids |
| CH5 | Neutral protease (Metalloprotease) | — | — | Nonterminal amino acids |
| CH6 | Neutral protease (Serine protease) | — | — | Nonterminal amino acids |
| CH7 | Neutral protease (Serine protease) | — | — | Nonterminal amino acids |
| CH8 | Neutral protease (Cysteine protease) | — | — | Nonterminal amino acids |
| CH9 | Neutral protease (Serine protease) | — | — | Nonterminal amino acids |
| CH10 | Collagenase | — | — | Nonterminal + terminal amino acids |
| H080 | Neutral protease (50.000 U/g) | Carboxy-peptidase (300-700 U/g) | Leucine aminopeptidase (500-1200 U/g) | Nonterminal + terminal amino acids |

GLP-1 Secretion by STC-1 Cells

STC-1 cells were incubated with different final concentrations (0.2, 0.5 and 1% dry matter in Hepes buffer at pH 7.4) of the different hydrolyzed collagen obtained after simulated gastrointestinal digestion (SGID). Supernatants were collected after 2 h of incubation. GLP-1 levels were determined by enzyme immunoassay and expressed in pg/ml. Data are expressed in mean (n=3)±standard deviation.

Cells were stimulated with 2, 5, or 10 mg/ml of enzyme (mixture). For all enzyme (mixtures), a dose-dependent increase was seen in GLP-1 secretion, with highest GLP-1 secretion for the 10 mg/ml condition. Hence, FIG. 1 shows the results for the 10 mg/ml concentration for comparison of the enzyme (mixtures).

In Vivo Mouse Model

The following mouse model was used to for determining Area Under the Curve (AUC) of blood glucose levels, insulin/blood glucose, plasma GLP-1 levels, and Plasma GIP levels. C57BL6/J Mice (male, 23-25 g, 8-week old) were randomized into the treatment groups (n=10 mice/group) according to their body weight.

Mice were fasted for 6 hours, after which an oral glucose tolerance test (OGTT) was performed. Mice were treated with either vehicle, test item H080 at 3 different concentrations (40 mg/kg, 400 mg/kg and 4 g/kg), and Sitagliptin as a positive control. 45 minutes after receiving the active ingredients, mice received an oral glucose load (2 g/kg of body weight). Blood glucose was measured in blood collected at time −45, 0, 15, 30, 60, 90 and 120 minutes after glucose load. Insulin was determined (by enzyme-linked immunosorbent assay, ELISA) in plasma collected 45 min before (−45 min) and 15 minutes after (+15 min) the glucose load. From this, the ratio insulin/glucose could be determined.

The plasma GLP-1 and GIP levels were assessed one week after the OGTT test. For this purpose, mice were fasted for 6 hours and treated with Sitagliptin (400 μg/mouse) to avoid the degradations of GLP-1 and GIP by the dipeptidyl peptidase 4 (DPP-IV). After 30 min, mice received vehicle or test item H080 in an amount of 4 g/kg body weight. 15 minutes or 30 minutes after receiving the active ingredients, mice were anesthetized and blood was sampled from the portal vein. Plasma GLP-1 and GIP levels were measured by ELISA.

The model in healthy mice demonstrates both prevention and treatment of high blood glucose (and other parameters related to hyperglycemia) following treatment with active ingredients.

Following a similar methodology as described for the healthy mice, a study was also conducted in obese mice which have naturally developed high blood glucose with a similar result.

Results

In Vitro GLP-1 Secretion

FIG. 1 shows the GLP-1 secretion in STC-1 cells following incubation with 10 mg/ml of hydrolyzed collagen, as obtained by hydrolysis with the enzyme (mixtures) provided in Table 1 under optimal processing conditions.

The hydrolyzed collagen denoted as H080 induced the largest GLP-1 secretion. As compared to the blank, H080 induced a 5800-fold increase in GLP-1 secretion. The increase in GLP-1 mediated by H080 was at least 2.5-fold larger than that mediated by the other enzyme (mixtures) in the comparative test.

The data indicate that the combination of a neutral protease (e.g. serine protease), a carboxypeptidase and an aminopeptidase (e.g. leucine aminopeptidase) induces by far the highest GLP-1 secretion as compared to other enzymes and enzyme combinations.

It was found that the mere combination of two or more enzymes (e.g. the combination of two neutral proteases in "CH3") is not sufficient to further promote the GLP-1 secretion as compared to the use of only one enzyme (e.g. a neutral protease in "CH1" or "CH2", among others).

It was found that the mere combination of an endoprotease (i.e. enzyme cleaving at nonterminal amino acids) and an exoprotease (i.e. enzyme cleaving at terminal amino acids) is not sufficient to further promote the GLP-1 secretion as compared to the use of only an endoprotease. For example, "CH12" comprises both endopeptidase and exopeptidase activity, but could not further promote GLP-1 secretion as compared to enzymes comprising only endopeptidase activity.

The results shown in FIG. 1 were reproduced with different batches of gelatin.

The results show that hydrolysis of collagen with a combination of two or more enzymes selected from a neutral protease, a carboxypeptidase, and an aminopeptidase is important for obtaining hydrolyzed collagen with strong potency in lowering glucose, such as induced by GLP-1.

In Vivo Glucose-Lowering Activity

FIG. 2 shows the blood glucose levels in mice following treatment with 40 mg/kg H080, 400 mg H080, 4 g/kg H080, and 400 µg/mouse Sitagliptin. A dose-dependent decrease in blood glucose was seen following treatment with H080. The highest dose of H080 had a similar blood glucose-lowering effect as the drug Sitagliptin. This shows that the hydrolyzed collagen may be provided as a safe alternative to pharmaceuticals drugs which are often associated with side effects.

FIG. 3 shows the ratio of insulin/blood glucose in mice following treatment with 40 mg/kg H080, 400 mg H080, 4 g/kg H080, and 400 µg/mouse Sitagliptin. H080 mediated a significant increase in the insulin/glucose ratio. A dose-dependent increase in insulin/glucose ratio was seen following treatment with H080.

In the healthy mouse model, mice receive active ingredients before the glucose load. The healthy mouse is therefore particularly suitable to study the prevention of hyperglycemia. A study was also conducted in obese mice which have naturally developed high blood glucose. The methodology was similar as described for the healthy mice. Since the obese mice already have an increased blood glucose when receiving the active ingredients, an improvement in blood glucose (and other parameters related to hyperglycemia) in the obese mouse model further strengthens the treatment of disease by active ingredients.

Figure 1:
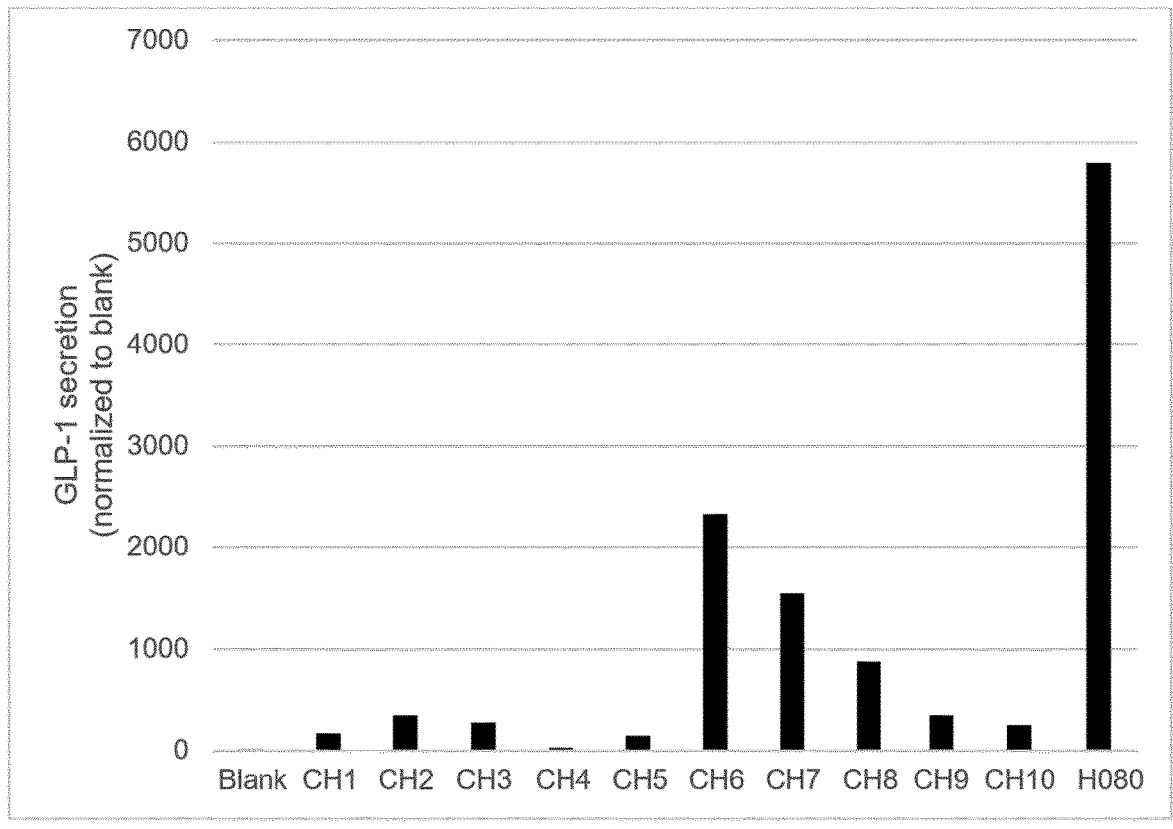
Figure 2:
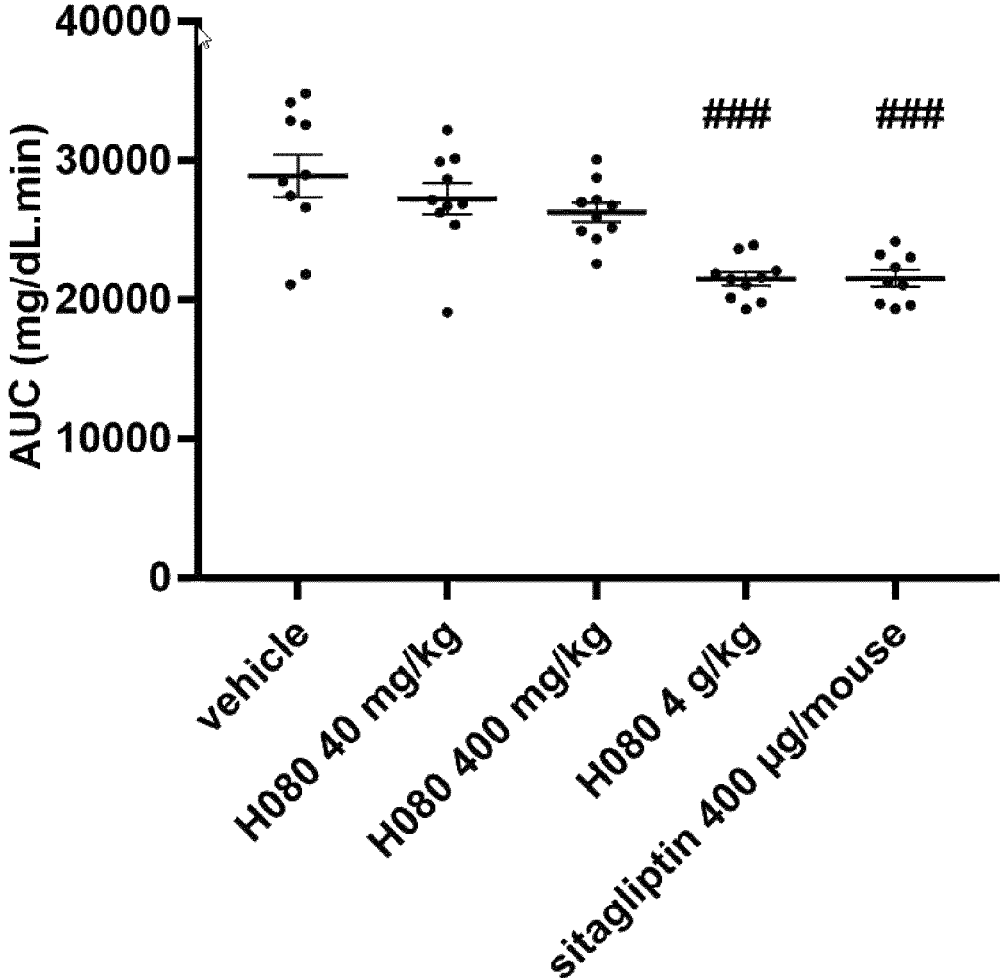
Figure 3:
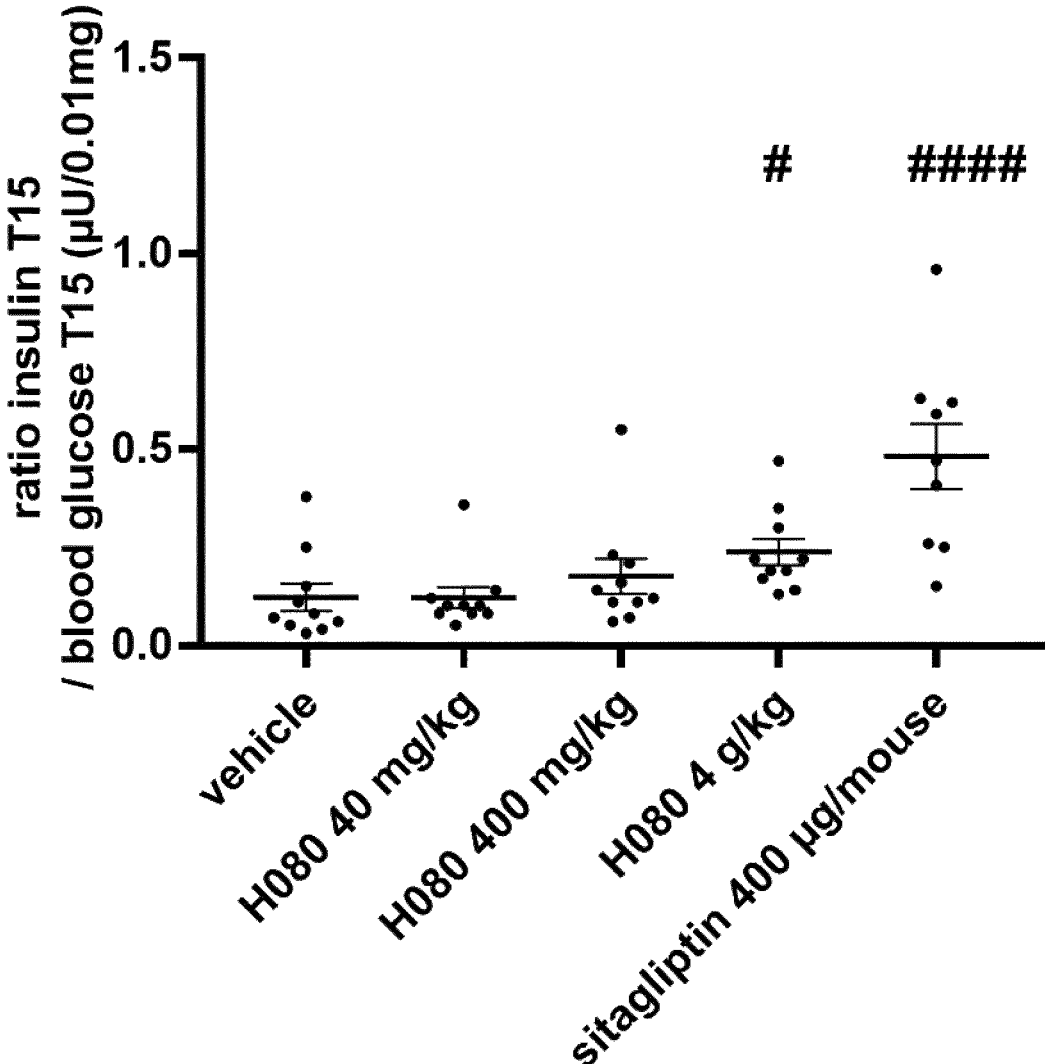
Figure 4:
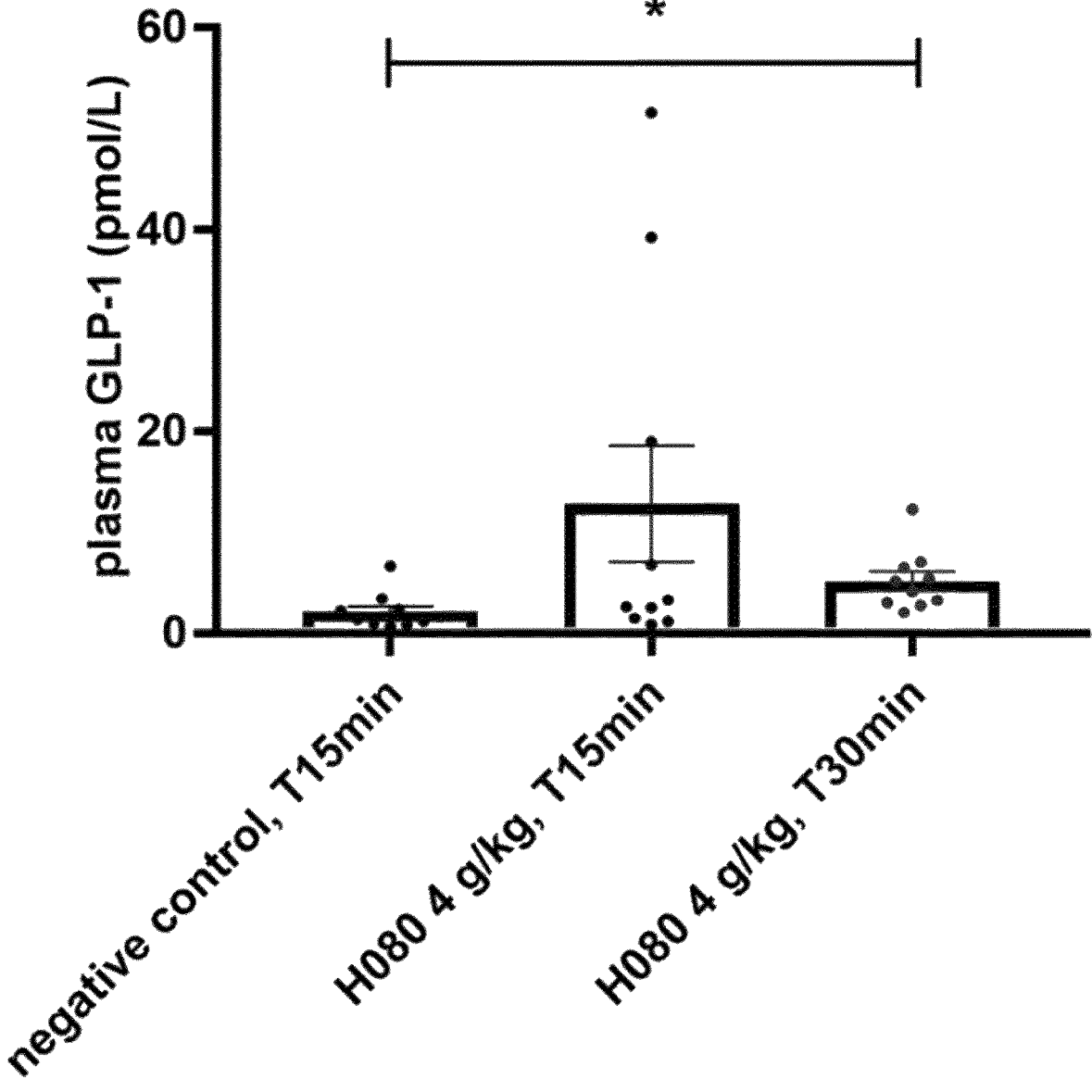
FIG. 4 shows the plasma GLP-1 levels following control treatment or following treatment with 4 g/kg H080. Treatment with H080 increased the plasma GLP-1 levels, wherein the effect was largest 30 min after intake of H080.
Figure 5:
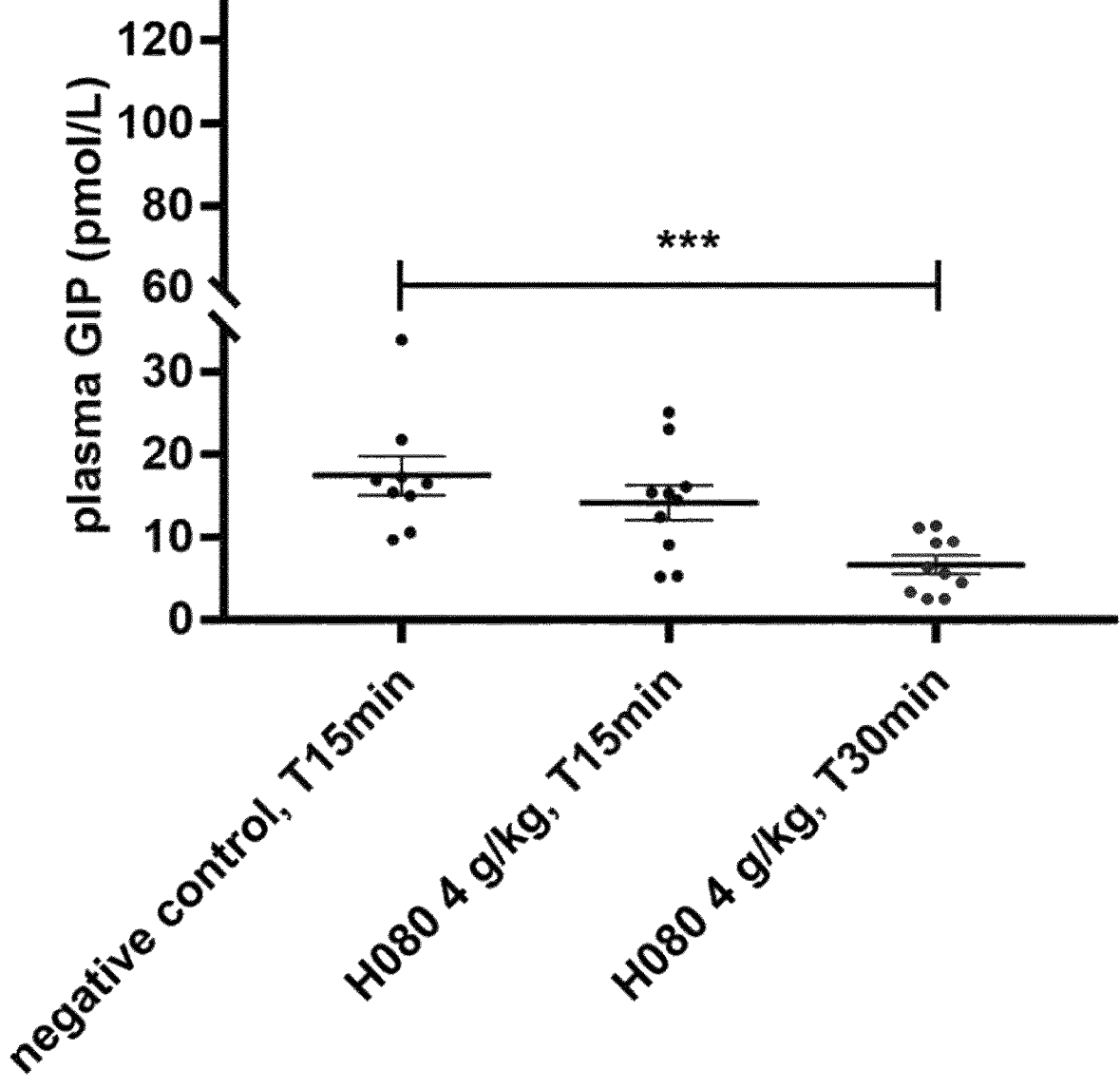
FIG. 5 shows the plasma GIP levels following control treatment or following treatment with 4 g/kg H080. Treatment with H080 decreased the plasma GIP levels, wherein the effect was largest 30 min after intake of H080.

Similar effects on the parameters studied in FIGS. 1-5 were observed in obese mice with high blood glucose. This further strengthens effective treatment of hyperglycemia (and related parameters) by H080.

Combination of Enzymes Chosen from a Neutral Protease, Carboxypeptidase and Aminopeptidase on Glucose-Lowering Activity The inventors found that high glucose-lowering activity (e.g. based on the GLP-1 secretion level) can be achieved when at least two enzymes are used in the enzymatic hydrolysis of the collagen-containing material, wherein the two enzymes are chosen from a neutral protease, a carboxypeptidase and an aminopeptidase.

As illustrated in Table 2, the use of a neutral protease in enzymatic hydrolysis of gelatin leads to a gelatin hydrolysate that has a glucose-lowering activity albeit limited. A combination of a neutral protease with a carboxypeptidase alone or an aminopeptidase alone provides a stronger glucose-lowering activity relative to the blank or the use of a neutral protease alone. The combination of all three enzymes leads to a gelatin hydrolysate with the highest glucose-lowering activity.

TABLE 2

| Group | Enzyme(s) used for hydrolysis of collagen and the effect of the hydrolysate on the lowering of glucose. | Glucose-lowering activity |
|---|---|---|
| I | Blank | Very low/absent |
| II | 1. Neutral protease (from *Aspergillus*) | Low |
| III | 1. Neutral protease (from *Aspergillus*) + 2. Carboxypeptidase (from *Aspergillus*) | High |
| IV | 1. Neutral protease (from *Aspergillus*) + 2. Aminopeptidase (from *Aspergillus*) | High |
| V | 1. Neutral protease (from *Aspergillus*) + 2. Carboxypeptidase (from *Aspergillus*) + 3. Aminopeptidase (from *Aspergillus*) | Very high |
| VI | 1. Neutral protease (from *Bacillus*) + 2. Carboxypeptidase (from *Aspergillus*) + 3. Aminopeptidase (from *Lactobacillus*) | Very high |

Characterization of Hydrolyzed Collagen with High Glucose-Lowering Activity

The hydrolyzed collagen with high glucose-lowering activity (e.g. group III-IV in Table 2) were characterized by a weight-average molecular weight of 1000-7000 Da and a polydispersity (weight average molecular weight/number average molecular weight) of 1.2-1.8 (average of ~1.56 was measured for >100 measurements), as determined by HPSEC.

Example 2

Example 2 shows the influence of the process conditions on obtaining hydrolyzed collagen for lowering blood glucose.

Methods

Gelatin hydrolysate was produced by hydrolysis using a combination of a neutral protease (50.000 U/g), an aminopeptidase (500-1200 U/g) and a carboxypeptidase (300-700 U/g) as described in Example 1.

A broad range of working conditions was tested, covering the conditions typically used in enzymatic hydrolysis.

The concentration of gelatin in the start solution was varied between 10-50 wt. %. The enzymes were used in a concentration of 2000 ppm for hydrolysis. The pH during enzymatic hydrolysis was varied between pH 4.0-10.0. The temperature during enzymatic hydrolysis was varied between 20-70° C.

Table 3 shows the influence of the gelatin concentration, pH, and temperature of enzymatic hydrolysis in obtaining gelatin hydrolysate fractions for lowering blood glucose in a preliminary test. The GLP-1 secretion was tested using the same methodology as in Example 1.

Table 4 shows the influence of the gelatin concentration, pH, and temperature of enzymatic hydrolysis in obtaining gelatin hydrolysate fractions for lowering blood glucose based on further elaborated, more extensive tests. The GLP-1 secretion was tested using the same methodology as in Example 1.

TABLE 3

Influence of the gelatin concentration, pH, and temperature
of enzymatic hydrolysis in obtaining gelatin hydrolysate fractions
for lowering blood glucose in a preliminary test.

| Process condition | | Suitable as blood glucose-lowering active ingredient |
|---|---|---|
| Gelatin wt. % | 10% | No |
| | 20% | Yes |
| | 30% | Yes |
| | 40% | Yes |
| | 50% | No |
| pH | pH 4 | No |
| | pH 5 | Yes |
| | pH 6 | Yes |
| | pH 8 | Yes |
| | pH 10 | No |
| Temperature | 20° C. | No |
| | 30° C. | Yes |
| | 40° C. | Yes |
| | 50° C. | Yes |
| | 60° C. | Yes |
| | 70° C. | No |

TABLE 4

Influence of the gelatin concentration, pH, and temperature of enzymatic
hydrolysis in obtaining gelatin hydrolysate fractions for lowering
blood glucose based on further elaborated, more extensive tests.

| Process condition | | Suitable as blood glucose-lowering active ingredient |
|---|---|---|
| Gelatin wt. % | 10% | ++ |
| | 20% | +++ |
| | 30% | +++ |
| | 35% | +++ |
| | 40% | ++ |
| | 45% | + |
| | 50% | + |
| pH | pH 4.0 | + |
| | pH 4.5 | + |
| | pH 5.0 | ++ |
| | pH 5.5 | +++ |
| | pH 6.0 | +++ |
| | pH 6.5 | +++ |
| | pH 7.0 | ++ |
| | pH 7.5 | ++ |
| | pH 8.0 | + |
| | pH 9.0 | + |
| | pH 10.0 | + |
| Temperature | 20° C. | + |
| | 30° C. | + |
| | 35° C. | + |
| | 40° C. | + |
| | 45° C. | +++ |
| | 50° C. | +++ |
| | 55° C. | ++ |
| | 60° C. | + |

+: less suitable;
++: more suitable;
+++: most suitable

As shown in Tables 3 and 4 collectively, it is found that a hydrolyzed collagen suitable for enhancing GLP-1 secretion can be achieved over a broad range of values for the precursor concentration (gelatin wt. %), pH, and temperature.

Regarding the precursor concentration (gelatin wt. %), satisfactory results were obtained over the entire range of 10-50 wt. % tested, with apparently an optimum at a concentration of 20-35 wt. %.

Regarding the pH, satisfactory results were obtained over the entire range of pH 4.0-10.0 tested, with apparently an optimum at pH 5.5-6.5.

Regarding the temperature, satisfactory results were obtained over the entire range of 20-60° C. tested, with apparently an optimum at 45-50° C.

The results show that hydrolysis performed at (excessive) high temperatures (e.g. at a temperature of 70° C. or higher) may not lead to a hydrolyzed collagen product suitable for enhancing GLP-1 secretion collagen. It is considered that this is the result of enzyme denaturation and subsequently impaired reaction rate.

The combination of preferred gelatin concentration, pH, and temperature may lead to best activity in enhancing GLP-1 secretion by STC-1 cells. As shown in Table 5, the combination of gelatin concentration of (30-40 wt. %), pH (6-7.5), and temperature (40-55° C.) leads to a surprisingly high activity of the gelatin hydrolysate in enhancing GLP-1 secretion by STC-1 cells. The GLP-1 secretion was tested using the same methodology as in Example 1.

TABLE 5

GLP-1 secretion by STC-1 cells stimulated with hydrolyzed
collagen obtained by a combination of a neutral protease,
carboxypeptidase and an aminopeptidase, wherein enzymatic
hydrolysis was performed at different process conditions.

| Process conditions | GLP-1 level |
|---|---|
| 30-40 wt. % gelatin, pH 6-7.5, 40-55° C. | 3471 pg/ml |
| 30-40 wt. % gelatin, pH 7.5-8.5, 55-65° C. | 346 pg/ml |

Example 3

Example 3 shows the molecular weight and molecular weight distribution of hydrolyzed collagen obtained by hydrolysis with different enzymes (mixtures), in relationship to the ability of the hydrolyzed collagens in stimulating GLP-1 secretion by STC-1 cells.

Table 6 shows the molecular weight and molecular weight distribution of hydrolyzed collagen formulations obtained with different enzymes, with their different abilities to stimulate GLP-1 secretion in STC-1 cells. The methodology used for hydrolysis and to evaluate GLP-1 secretion was the same as described in Example 1.

"H080" was produced by hydrolysis using a combination of a neutral protease (50.000 U/g), an aminopeptidase (500-1200 U/g) and a carboxypeptidase (300-700 U/g) as described in Example 1. The collagen hydrolysates "CH11-CH19" were obtained by hydrolysis with either a neutral, alkaline or acid protease.

An "average" GLP-1 secretion was considered if the GLP-1 secretion was at least 1000-fold increased compared to stimulation with a blank control.

As can be seen from Table 6, "H080" induced ~6000-fold increased GLP-1 secretion compared to stimulation with a blank control and is considered as "very high" GLP-1 secretion. Hydrolyzed collagens according to groups "CH11-CH19"—i.e. obtained by hydrolysis with either a neutral, alkaline or acid protease-show no/little or only average GLP-1 secretion.

As can be seen from Table 6, "H080" is characterized by a weight average molecular weight of ~3000 Da (or mean average molecular weight of ~2000 Da). "H080" is furthermore characterized by a high fraction of collagen peptides (i.e. ~47.2%) falling in the 2-5 kDa range. "H080" is furthermore characterized by high stimulatory activity on GLP-1 secretion (i.e. ~6000-fold increase compared to the blank control group). The "CH11-CH19" groups lack one or more of these features.

TABLE 6

Overview of enzyme (mixtures) used for hydrolysis of collagen, molecular
weight and molecular weight distribution of the obtained hydrolyzed collagen,
and their ability to stimulate GLP-1 secretion in STC-1 cells.

| Group name | GLP-1 secretion Relative to blank | Mn (Da) | Mw (Da) | Pd | Molecular weight distribution (%) | | | | |
|---|---|---|---|---|---|---|---|---|---|
| | | | | | <1 kDa | 1-2 kDa | 2-5 kDa | 5-10 kDa | >10 kDa |
| CH11 Neutral protease (serine protease) | No/low | 1391 | 2007 | 1.4 | 18.4 | 46.8 | 30.3 | 4.2 | 0.3 |
| CH12 Neutral protease (serine protease) | No/low | 2131 | 3972 | 1.9 | 7.9 | 24.9 | 40.2 | 21.1 | 5.9 |
| CH13 Neutral protease (metallo protease) | No/low | 3842 | 7764 | 2.0 | 3 | 8.8 | 26.9 | 33.9 | 27.5 |
| CH14 Alkaline protease (metallo protease) | Average | 1664 | 2602 | 1.6 | 13.3 | 36 | 40 | 9.8 | 0.9 |
| CH15 Alkaline protease (serine protease) | No/low | 2652 | 6078 | 2.3 | 5.5 | 14.9 | 36.3 | 25.3 | 18 |
| CH16 Alkaline protease (serine-/metallo protease) | No/low | 3289 | 6681 | 2.0 | 2.9 | 12 | 31.7 | 30.8 | 21.7 |
| CH17 Alkaline protease (collagenase) | No/low | 1119 | 1484 | 1.3 | 27 | 55.8 | 16.8 | 0.4 | 0.1 |
| CH18 Alkaline protease (serine protease) | Average | 1425 | 2055 | 1.4 | 17.5 | 47.8 | 30.5 | 3 | 1.2 |
| CH19 Acid protease (cysteine protease) | No/low | 1333 | 1852 | 1.4 | 20.5 | 47.2 | 30 | 2.4 | 0 |
| H080 Neutral protease + Carboxypeptidase + Leucine aminopeptidase | Very high | 1933 | 3063 | 1.6 | 8.7 | 28.8 | 47.2 | 14.4 | 0.9 |

The invention claimed is:

1. A method for lowering blood glucose level in a human subject in need thereof, comprising administering a hydrolyzed collagen to the human subject, wherein the hydrolyzed collagen is obtained by enzymatic hydrolysis of a collagen-containing material with a combination of enzymes comprising a neutral protease and one or both of a carboxypeptidase, and an aminopeptidase, wherein the hydrolyzed collagen is administered in an effective amount as one or more unit doses of at least 0.5 g per day and wherein the total daily dose is not more than 30 g, wherein the amount is the dry weight amount.

2. The method according to claim 1, wherein the combination of enzymes comprises a neutral protease, a carboxypeptidase, and an aminopeptidase.

3. The method according to claim 1, wherein the method is selected from the group consisting of:

increasing blood glucagon-like peptide-1;
decreasing blood glucagon;
increasing blood insulin; and
increasing blood insulin/glucose ratio.

4. The method according to claim 1, wherein the collagen-containing material is gelatin.

5. The method according to claim 1, wherein the hydrolyzed collagen is administered at a daily dose in an amount of 1-100 gram, or in an amount of 2-50 gram, wherein the amount is the dry weight amount.

6. The method according to claim 1, wherein the hydrolyzed collagen has a weight average molecular weight of 2000-4000 Da, or 2500-3500 Da; and comprises 35-60% by weight of collagen peptides with a molecular weight in the range of 2000-5000 Da, calculated on total weight of collagen peptides in the hydrolyzed collagen.

7. The method according to claim 1, wherein the method is for ameliorating postprandial glucose.

8. The method according to claim 1, wherein the method is for ameliorating hyperglycemia or a risk factor for hyperglycemia.

9. The method according to claim 8, wherein the risk factor for hyperglycemia is one or more selected from the group consisting of insulin resistance, type 2 diabetes, gestational diabetes, high body mass index, obesity, and hyperglucagonemia.

* * * * *